(12) United States Patent
Collins et al.

(10) Patent No.: US 11,351,120 B2
(45) Date of Patent: Jun. 7, 2022

(54) USE OF HIGHER DOSES OF MODIFIED RELEASE HUPERZINE FORMULATIONS

(71) Applicant: SUPERNUS PHARMACEUTICALS, INC., Rockville, MD (US)

(72) Inventors: Stephen D. Collins, Lake Forest, IL (US); Peter J. Goldstein, Hollywood, FL (US); Joshua T. Johnstone, Apex, NC (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 16/688,916

(22) Filed: Nov. 19, 2019

(65) Prior Publication Data

US 2020/0155456 A1 May 21, 2020

Related U.S. Application Data

(60) Provisional application No. 62/769,475, filed on Nov. 19, 2018.

(51) Int. Cl.
*A61K 9/16* (2006.01)
*A61K 31/439* (2006.01)
*A61P 25/08* (2006.01)

(52) U.S. Cl.
CPC .......... *A61K 9/1676* (2013.01); *A61K 31/439* (2013.01); *A61P 25/08* (2018.01)

(58) Field of Classification Search
None
See application file for complete search history.

(56) References Cited

U.S. PATENT DOCUMENTS

| | | |
|---|---|---|
| 8,193,212 B2 | 6/2012 | Schachter |
| 2006/0045865 A1 | 3/2006 | Jacob et al. |
| 2011/0224245 A1* | 9/2011 | Schachter ............ A61K 31/402 514/291 |
| 2013/0040982 A1 | 2/2013 | Friedman et al. |
| 2015/0335624 A1 | 11/2015 | Collins et al. |
| 2016/0136103 A1 | 5/2016 | Boudy et al. |
| 2016/0206602 A1 | 7/2016 | Reynolds |

FOREIGN PATENT DOCUMENTS

| | | | |
|---|---|---|---|
| CN | 1208054 C | | 6/2005 |
| CN | 1751683 A | | 3/2006 |
| CN | 101081217 | * | 12/2007 |
| CN | 101081217 A | | 12/2007 |
| CN | 1682719 B | | 4/2010 |
| CN | 101732312 A | | 6/2010 |
| CN | 1726911 B | | 8/2010 |
| CN | 101264058 B | | 9/2010 |
| CN | 101485640 B | | 3/2011 |
| CN | 101485639 B | | 4/2011 |
| CN | 102512395 B | | 10/2013 |
| ES | 2351709 T3 | | 2/2011 |
| WO | WO 2004/037190 | * | 5/2004 |
| WO | WO-2012/006961 A1 | | 1/2012 |
| WO | WO 2012129759 | * | 10/2012 |
| WO | WO-2013/139195 A1 | | 9/2013 |
| WO | WO 2014107685 | * | 7/2014 |

OTHER PUBLICATIONS

Biscayne Neurotherapeutics Reports Successful Phase 1b Clinical Trial Results for Its Novel Antiepileptic Agent 2017.*
Drugs & Therapy Bulletin 2007.*
CN 101081217 Machine Translatio (Year: 2007).*
Chu et al., "Pharmacokinetics of Huperzine A in Dogs Following Single Intravenous and Oral Administrations," Planta Med, 2006, 72(6):552-555.
International Search Report in PCT PCT/US2018/033722 dated Sep. 20, 2018.
Gao et al., "Controlled release of huperzine A from biodegradable microspheres: In vitro and in vivo studies," International Journal of Pharmaceutics, 2007, 330:1-5.
Liu et al., "Preparation and in vitro and in vivo release studies of Huperzine A loaded microspheres for the treatment of Alzheimer's disease," Journal of Controlled Release, 2005, 107:417-427.
SURELEASE product information (year: 2016).
SURELEASE Application Data, Corolcon, 2011, 1-5.

* cited by examiner

*Primary Examiner* — Danah Al-Awadi
(74) *Attorney, Agent, or Firm* — Foley & Lardner LLP

(57) ABSTRACT

The present application discloses pharmaceutical compositions and methods of treating neurological disorders and seizure disorders with the high dose modified release compositions of huperzine. The pharmaceutical compositions and methods described herein, allow for higher dosing of huperzine, while avoiding rapid peak plasma levels, thereby avoiding the dose-limiting adverse events associated with the immediate release formulations.

12 Claims, 7 Drawing Sheets

USE OF HIGHER DOSES OF MODIFIED RELEASE HUPERZINE FORMULATIONS

SUMMARY OF THE INVENTION

Huperzine A is a naturally occurring sesquiterpene alkaloid compound found in the firmoss Huperzia serrata. It is a potent inhibitor of acetylcholinesterase. In several countries, Huperzine A is sold as a dietary supplement for memory support. In China, huperzine A is an approved by the China Drug Administration (CDA) for the treatment of dementia.

Huperzine A has been administered to healthy volunteers and patients in numerous trials, many in China, demonstrating acceptable safety and tolerability as well as efficacy in Alzheimer's disease, benign senescent forgetfulness, vascular dementia, myasthenia gravis, schizophrenia, and cocaine dependence. The dosages used in these trials were between 0.01 and 0.8 mg/day via oral administration or intramuscular injection. While these studies showed a favorable safety profile, in some studies, transient dose related nausea occurred at the higher dose levels.

Applicants conducted a dose escalation study in patients with drug-resistant epilepsy, to investigate the safety and tolerability of an immediate release formulation of huperzine A. In this study, patients experienced dose-limiting adverse events (nausea and vomiting), many within the first 31 hours, most probably due to the rapid plasma exposure of the immediate release formulation (vide infra).

While huperzine A could potentially provide additional beneficial effects in the areas of neurological disorders, seizure disorders, memory and language impairment, immediate release formulations of huperzine A are inadequate for treating disorders where higher therapeutic thresholds are needed due to dose-related adverse events, especially in patients with chronic conditions. Immediate release formulations also have the added drawback of requiring dosing 4 to 6 times daily due to the short half-life ($t_{1/2}$) associated with these formulations. Dosing 4 to 6 times daily is unacceptable in many patient populations, for example, those with memory loss or seizures, as compliance becomes a major issue for these patients. Nonclinical studies suggest that higher doses than those used previously, such as up to 6.4 mg/day, may be safe if delivered with a formulation that reduces fluctuations in peak to trough plasma levels.

A slow release pill containing Huperzine A has been reported by Zhou et al. in the Chinese patent application CN101081217, however, these formulations fail to significantly reduce peak plasma concentrations compared with immediate release formulations and also fail to extend the time to maximum plasma concentration (Tmax). As a result, these formulations would not overcome the serious adverse events associated with high peak plasma concentrations and would require dosing 4-6 times a day, thus offering little to no advantage over immediate release formulations.

The present invention allows for the use of higher doses of Huperzine providing improved efficacy, compared to the previously used lower doses, while maintaining a desirable safety profile not attainable with previously known formulations.

Embodiments of the present invention relate to modified release pharmaceutical composition for oral delivery of huperzine that may be used to treat the various neurological disorders and diseases, for example, pain, Alzheimer's disease, and seizure disorders. The compositions provide for modified release formulations that allow for optimal efficacy of huperzine without the dose-limiting adverse events associated with immediate release formulations.

Embodiments of the invention are directed to a pharmaceutical composition for oral delivery comprising: (a) about 74 to 86 weight % of a sugar sphere core wherein the sugar sphere has a particle size of about 500-710 µm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % huperzine, and one or more excipients, wherein the total amount of excipients is about 5 weight % to about 9 weight %; and (c) about 7 weight % to 16 weight % of a plasticized ethyl cellulose polymer layer coating the huperzine layer, wherein the huperzine layer comprises a therapeutically-effective amount of huperzine. In some embodiments the huperzine is huperzine A or a pharmaceutically acceptable salt thereof.

Some embodiments of the invention are directed to a pharmaceutical composition comprising: (a) about 80 weight % to about 83 weight % of a sugar sphere core wherein the sugar sphere core has a particle size of about 500-710 µm; (b) a huperzine layer coating the sugar sphere, wherein the huperzine layer comprises about 0.95 weight % to about 1 weight % huperzine A or a pharmaceutically acceptable salt of huperzine A that is equivalent to about 0.95 weight % to about 1 weight % huperzine A, about 5 weight % to about 6 weight % hydroxypropyl methylcellulose, and about 0.95 weight % to about 1 weight % polyvinylpyrrolidone; and (c) about 8 weight % to about 12 weight % of a plasticized ethyl cellulose polymer layer coating the huperzine layer, wherein the huperzine layer comprises a therapeutically effective amount of huperzine A.

Some embodiments of the present invention are directed to a pharmaceutical composition characterized by a maximum plasma concentration ($C_{max}$) of huperzine A in plasma of about 4 ng/mL to about 8 ng/mL, a $T_{max}$ of about 4 hours to about 8 hours and a $t_{1/2}$ of about 8 hours to about 12 hours, upon oral administration of a therapeutically effective dose of the composition to a human subject. In one embodiment the $C_{max}$ is about 4 ng/mL to about 6 ng/mL, $T_{max}$ is about 4 hours to about 8 hours and the $t_{1/2}$ is about 10 hours to about 12 hours. In one embodiment the $C_{max}$ is about 6 ng/mL, the $T_{max}$ is about 4 hours and the $t_{1/2}$ is about 8.3 hours.

Some embodiments of the invention are to a pharmaceutical composition comprising a therapeutically-effective amount of huperzine A, characterized by a $T_{max}$ of about 4-8 hours and a $C_{max}$ that is reduced by about 25% to about 75% when compared with a $C_{max}$ of an immediate release huperzine formulation administered at an equivalent dose. In some embodiments the $C_{max}$ is reduced by 50%.

Some embodiments of the present invention are directed to a pharmaceutical composition that exhibits the following dissolution profile when tested according to USP type 1 dissolution apparatus at 50 revolutions per minute in 50 mM phosphate buffer (pH 6.8) at 37° C.: about 36% to about 46% of the huperzine is released after 2 hours, about 61% to about 77% of the huperzine is released after 4 hours, about 84% to about 97% of the huperzine is released after 8 hours and not less than about 89% of the huperzine is released after 12 hours.

Some embodiments of the invention describe a method of treating a neurological disorder or a seizure disorder comprising administering a pharmaceutical composition according to any embodiment described herein. In some embodiments, the composition is administered twice daily. In some embodiments the seizure disorder is epilepsy, i.e. repetitive seizures—for example Focal Impaired Awareness Seizures (FIAS)—with or without loss of consciousness, previously known as Complex Partial Seizures (CPS).

Some embodiments of the invention describe a method of treating a disorder selected from the group consisting of a neurological disorder and a seizure disorder, in a patient in need thereof, wherein the patient has a better side effect profile, comprising administering one or more titration doses of huperzine A, followed by administering a maintenance dose of huperzine A; wherein the huperzine A is administered in a modified release formulation of huperzine. In some embodiments the modified release formulation of huperzine is a pharmaceutical composition according to any embodiment described herein.

Some embodiments of the invention describe a method of reducing the frequency of seizures in a patient in need thereof, comprising administering to the patient, one or more titration doses of the pharmaceutical composition followed by administering a maintenance dose of the pharmaceutical composition, wherein the titration dose comprises about 0.5 mg administered twice a day (BID) to about 2.5 mg BID; and wherein the maintenance dose comprises about 3.0 mg BID to about 4.0 mg BID. In some embodiments, the patient has a reduction in the frequency of seizures greater than about 75%.

Some embodiments of the invention describe a method of reducing the frequency of seizures in a patient in need thereof, comprising administering to the patient a pharmaceutical composition comprising a therapeutically effective amount of huperzine. In some embodiments, the therapeutically effective amount of huperzine about 3.0 mg to about 4.0 mg BID.

Some embodiments of the invention describe a method of treating a neurological disorder and a seizure disorder, in a patient in need thereof, wherein the patient has a better side effect profile and/or reduced frequency of seizures, comprising administering a dosing regimen including about 0.25 mg to about 0.75 mg BID on days 1 to 16; about 0.75 mg to about 1.75 mg, BID on days 17 to 40; about 1.75 mg to about 2.5 mg BID on days 41 to 90; and about 2.5 mg to about 3.0 mg BID on days 91 to 180.

Some embodiments of the invention describe a method of treating a neurological disorder and a seizure disorder, in a patient in need thereof, wherein the patient has a better side effect profile and/or reduced frequency of seizures, comprising administering to the said patient a dosing regimen including 0.25 mg to about 0.75 mg BID on days 1 to 16; about 0.75 mg to about 1.75 mg BID on days 17 to 40; about 1.75 mg to about 2.5 mg BID on days 41 to 90; and 2.5 nag to about 3.0 mg BID Oil days 91 to 180 and about 3.0 mg to about 4.0 mg BID on days 181 to 270.

Some embodiments of the invention describe a method of treating a neurological disorder and a seizure disorder, in a patient in need thereof, wherein the patient has a better side effect profile and/or reduced frequency of seizures, comprising administering to the said patient one or more titration doses of the pharmaceutical composition followed by administering a maintenance dose of the pharmaceutical composition, wherein the titration dose comprises about 0.5 mg BID to about 2.5 mg BID; and wherein the maintenance dose comprises about 3.0 mg BID to about 4.0 mg BID.

Some embodiments of the invention describe a method of treating a neurological disorder and a seizure disorder, in a patient in need thereof, wherein the patient has a better side effect profile, comprising administering a first dosing regimen of at least one dosing regimen selected from a. to i. (as further described below) and administering a second dosing regimen of at least one dosing regimen selected from j. to o. (as further described below), provided the second dosing regimen ascends from the first dosing regimen and further provided the last dosing regimen is the maintenance dose and therefore will be administered for as long as the patient is in need of the treatment thereof:

a. optionally administering a dose of about 0.25 mg of huperzine A, once every about 12 hours for at least two days and up to two weeks;
b. optionally administering a dose of about 0.5 mg of huperzine A, once every about 12 hours for at least two days and up to two weeks;
c. optionally administering a dose of about 0.75 mg of huperzine A, once every about 12 hours for at least two days and up to two weeks;
d. optionally administering a dose of about 1 mg of huperzine A, once every about 12 hours for at least two days and up to two weeks;
e. optionally administering a dose of about 1.25 mg of huperzine A, once every about 12 hours for at least two days and up to two weeks;
f. optionally administering a dose of about 1.5 mg of huperzine A, once every about 12 hours for at least two days and up to two weeks;
g. optionally administering a dose of about 1.75 mg of huperzine A, once every about 12 hours for at least two days and up to two weeks;
h. optionally administering a dose of about 2 mg of huperzine A, once every about 12 hours for at least two days;
i. optionally administering a dose of about 2.5 mg of huperzine A, once every about 12 hours for at least two days;
j. optionally administering a dose of about 2.75 mg of huperzine A, once every about 12 hours for at least two days;
k. optionally administering a dose of about 3.0 mg of huperzine A, once every about 12 hours for at least two days;
l. optionally administering a dose of about 3.25 mg of huperzine A, once every about 12 hours for at least two days;
m. optionally administering a dose of about 3.5 mg of huperzine A, once every about 12 hours for at least two days;
n. optionally administering a dose of about 3.75 mg of huperzine A, once every about 12 hours for at least two days;
o. optionally administering a dose of about 4.0 mg of huperzine A, once every about 12 hours for at least two days;

wherein the huperzine A of a.-o. is administered in a modified release formulation of huperzine A. In some embodiments the modified release formulation of huperzine A is a pharmaceutical composition according to any embodiment described herein.

Some embodiments describe a method of treating a disorder selected from the group consisting of a neurological disorder and a seizure disorder, to a patient in need thereof, wherein the patient has a better side effect profile, comprising administering a modified release formulation of huperzine A, wherein the modified release formulation of huperzine A is characterized in healthy subjects by an average plasma concentration at steady state ($C_{ss}$) of huperzine A selected from the group consisting of: about 0.52 to about 0.82 ng/mL at a 0.25 mg dose; about 1.91 to about 2.99 ng/mL at a 0.50 mg dose; about 3.56 to about 5.55 ng/mL at a 0.75 mg dose; about 5.58 to about 8.72 ng/mL at a 1 mg dose; about 8.22 to about 12.84 ng/mL at a 1.25 mg dose; about 9.02 to about 14.09 ng/mL at a 1.5 mg dose; about 10.04 to about 15.69 ng/mL at a 1.75 mg dose; about 16 to about 25 ng/mL at a 2.0 mg dose; and about 18.48 to about 28.88 ng/mL at a 2.5 mg dose; about 25.2 ng/ml at a 2.75 mg dose; about 27.8 ng/mL at a 3.0 mg dose; about 30.3 ng/mL at a 3.25 mg dose; about 32.9 ng/mL at a 3.50 mg dose; about 35.5 ng/mL at a 3.75 mg dose; and about 38.0 ng/mL at a 4.0 mg dose.

Some embodiments describe a method of treating a disorder selected from the group consisting of a neurological disorder and a seizure disorder, to a patient in need thereof, wherein the patient has a better side effect profile and/or reduced frequency of seizures, comprising administering a modified release formulation of huperzine A, wherein the modified release formulation of huperzine A is characterized by a $C_{ss}$ of huperzine A in plasma of at least 8 ng/mL when administered at a therapeutically effective dose.

DETAILED DESCRIPTION

Definitions

Figure 1:
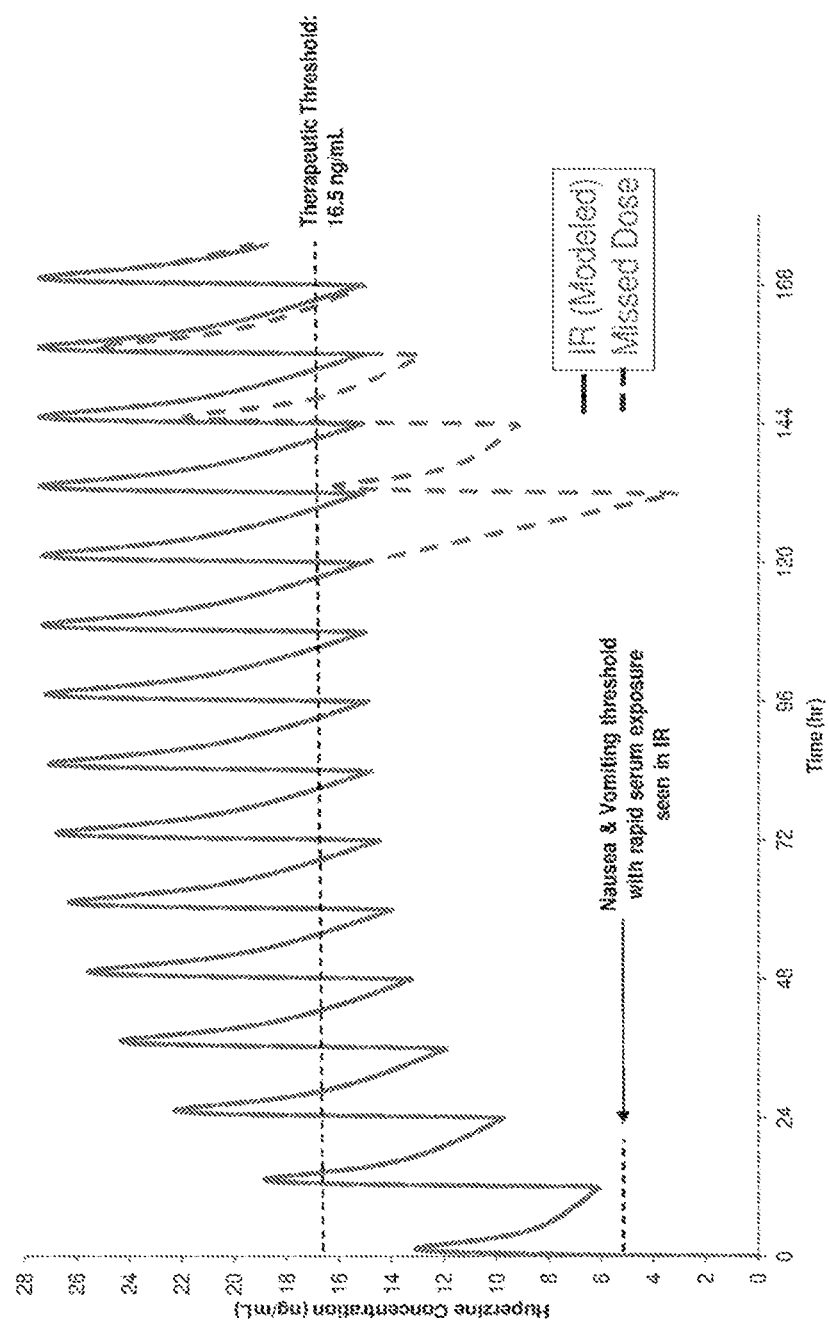
FIG. 1 shows the modeled plasma levels of huperzine A following immediate release dosing for an example titration schedule of 2 mg BID.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "symptom" is a reference to one or more symptoms and equivalents thereof known to those skilled in the art, and so forth.

As used herein, the term "about" means plus or minus 10% of the numerical value of the number with which it is being used. Therefore, about 50 mL means in the range of 45 mL-55 mL.

The term "administering" or "administration" and the like, refers to providing the compositions of the invention (e.g. a composition according to any embodiment described herein) to a subject in need of treatment. Preferably the subject is a mammal, more preferably a human. The present invention comprises administering a composition according to any embodiment described herein, alone or in conjunction with another therapeutic agent. When a composition according to any embodiment described herein, is administered in conjunction with another therapeutic agent, the composition and the other therapeutic agent can be administered at the same time or different times.

"Adverse event" as used herein refers to any untoward medical occurrence in a patient or clinical investigation participant administered a pharmaceutical product and which does not necessarily have a causal relationship with this treatment. For example, an adverse event may cause the subject discomfort and (a) interrupts the subject's usual activities, (b) causes considerable interference with the subject's usual activities, and may be incapacitating or life threatening, (c) is life threatening to the subject, (d) results in dose limiting toxicity or (e) requires additional medication to combat the adverse event, or combinations thereof. For example, if the subject experiences nausea, vomiting and/or diarrhea upon administration of a huperzine formulation that requires the administration of an antiemetic in order to continue to take the huperzine formulation, the subject has a dose-limiting adverse event. If the subject experiences life threatening event, requires hospitalization, has a medically significant event, an event that results in persistent or significant disability or incapacity, or an event that results in death, the subject has a serious adverse event.

"Amyloid-related disorders" as used herein, include diseases associated with the accumulation of amyloid which can either be restricted to one organ, "localized amyloidosis", or spread to several organs, "systemic amyloidosis". Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, type II diabetes and any related disorders thereof, neurodegenerative diseases such as scrapie, bovine spongiform encephalitis, Creutzfeldt-Jakob disease, Alzheimer's disease, senile systemic amyloidosis (SSA), Cerebral Amyloid Angiopathy, Parkinson's disease, and prion protein related disorders (e.g. prion-related encephalopathies), and rheumatoid arthritis.

The phrase "better side effect profile" means that the side effect(s) experienced by the patient or group of patients upon treatment with the modified release formulation of huperzine (1) occur at a lower incidence, (2) occur for a shorter duration, or (3) decrease in severity, or combinations thereof; compared to immediate release formulations of huperzine.

The term "$C_{max}$" is the peak plasma concentration of a drug after administration to a subject.

The term "dose" as used herein refers to the quantity of active compound, for example huperzine or huperzine A absent of any inactive ingredients or salts.

As used herein, the term "effective amount" means the amount of a drug or pharmaceutical agent, or the amount of a combination of drugs or pharmaceutical agents that will elicit the biological or medical response of a tissue, system, animal or human that is being sought, for instance, by a researcher or clinician.

As used herein, the term "epilepsy" refers to a disorder of the brain characterized by an enduring predisposition to generate epileptic seizures and by the neurobiological, cognitive, psychological, and social consequences of this condition. An epileptic seizure is a transient occurrence of signs and/or symptoms due to abnormal excessive or synchronous neuronal activity in the brain.

It will be understood by one of skill in the art that the term "plasticized ethylcellulose" is also known by non-proprietary names, for example, "plasticized ethyl cellulose"; synonyms and several brand names, for example, "Surelease®".

It will be understood by one of skill in the art that the term "hydroxypropyl methylcellulose" is also known by many non-proprietary names, for example, "HPMC", "hydroxypropylmethylcellulose", "hypromellosum", and "hypromellose"; synonyms; and several branded names, for example, Methocel™.

The term "huperzine" means huperzine A, huperzine B, or huperzine C, or their pharmaceutically accepted salts or solvates thereof, unless otherwise defined in a particular embodiment. Huperzine A is (1R,9S,13E)-1-amino-13-ethylidene-11-methyl-6-azatricyclo[7.3.1.02,7]trideca-2(7),3,10-trien-5-one. Huperzine B is (4aR,5R,10bR)-2,3,4,4a,5,6-hexahydro-12-methyl-1H-5,10b-propeno-1,7-phenanthrolin-8(7H)-one. Huperzine C is (1R,9S,13R)-1-amino-13-ethenyl-11-methyl-6-azatricyclo[7.3.1.02,7]trideca-2(7),3,10-trien-5-one.

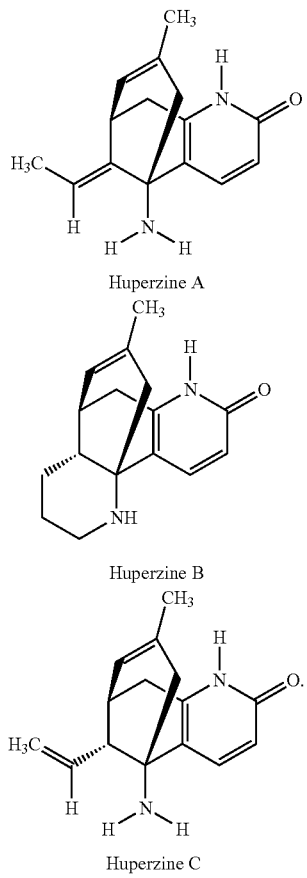

Huperzine A

Huperzine B

Huperzine C

Preferably, huperzine is huperzine A in any embodiment described herein.

The term "maintenance dose" as described herein refers to a dose of huperzine that is administered to maintain a desired level of the medication in the blood. In some embodiments the maintenance dose is the therapeutically effect amount.

The term "modified release formulation of huperzine" refers to any oral formulation of huperzine wherein the huperzine-release characteristics of time, course and/or location are chosen to accomplish therapeutic or convenience objectives not offered by immediate release huperzine.

The term "neurological disorder" includes, but is not limited to, an amyloid-related disorder such as Alzheimer's disease and the amyloid-disorders described herein, psychiatric disorders such as Tourette's syndrome, posttraumatic stress disorder (PTSD), panic and anxiety disorders, obsessive-compulsive disorder, and schizophrenia, developmental disorders such as fragile X syndrome and autism, pain, drug addictions such as alcoholism, neurodegenerative diseases such as Parkinson's disease and Huntington's disease, as well as stroke and ischemic brain injury, amyotrophic lateral sclerosis, and epilepsy. "Neurological disorder" also includes any disorder, symptom, or effect associated with or relating to exposure to a neurotoxin, including but not limited to neurotoxins such as chemical warfare agents.

The term "patient" or "subject" is used throughout the specification within context to describe an animal, generally a mammal and preferably a human, to whom treatment, including prophylactic treatment (prophylaxis), with the pharmaceutical compositions according to any embodiment described herein. For treatment of those infections, conditions or disease states which are specific for a specific animal such as a human patient, the term patient refers to that specific animal.

By "pharmaceutically acceptable" it is meant that the carrier, diluent or excipient must be compatible with the other ingredients of the formulation and not deleterious to the recipient thereof.

The term "pharmaceutically acceptable salt of huperzine that is equivalent to about 1 weight % huperzine" refers to a pharmaceutically acceptable salt of huperzine that would provide about 1 weight % of huperzine A free base if the salt was converted to huperzine. Similarly the terms "pharmaceutically acceptable salt that is equivalent to about 0.5 weight % to about 1.5 weight % huperzine", "pharmaceutically acceptable salt that is equivalent to about 0.9 weight % to about 1 weight % huperzine", "pharmaceutically acceptable salt that is equivalent to about 0.95 weight % to about 1 weight % huperzine" and the like refer to a pharmaceutically acceptable salt of huperzine that would provide about 0.5 weight % to about 1.5 weight %, about 0.9 weight % to about 1 weight %, about 0.95 weight % to about 1 weight %, huperzine free base respectively, if the salt was converted to huperzine. For example, 6 grams of huperzine A is needed to provide 1 weight % of a 600 g pharmaceutical formulation, but 6.89 g of the HCl salt of huperzine A is needed to provide 1 weight % huperzine A.

It will be understood by one of skill in the art that the term "polyvinylpyrrolidone" is also known by several non-proprietary names, for example, "PVP" "polyvinyl pyrrolidone", "povidone", and "polyvidone". It will also be understood that polyvinylpyrrolidones are referred to by their K number which indicates the mean molecular weight of the polyvinylpyrrolidone. Examples of polyvinylpyrrolidones include, but are not limited to polyvinylpyrrolidone K30, polyvinylpyrrolidone K10, polyvinylpyrrolidone K360, polyvinylpyrrolidone K40.

As used herein, the term "seizure disorder" means any condition in which one or more seizures is a symptom. As used herein, a seizure may be due to unusual electrical activity in the brain or may be a non-epileptic seizure, which is not accompanied by abnormal electrical activity in the brain. A seizure may be caused by, for example, but not limited to, psychological issues, psychological stress, trauma, hypoglycemia, low blood sodium, fever, alcohol use, or drug use or unknown causes. Types of seizures and seizure disorders include, but are not limited to, epilepsy (including intractable epilepsy), generalized seizures, primary generalized seizures, absence seizures, myoclonic seizures, partial seizures, complex partial seizures with or without generalization (for example, focal impaired awareness seizures (FIAS)), Lennox-Gastaut Syndrome, Dravet Syndrome and Generalized Epilepsy with Febrile Seizures plus (GEFS+). In some embodiments, the seizure disorder is epilepsy.

As used herein, the term "therapeutic" means an agent utilized to treat, combat, ameliorate, prevent, or improve an unwanted condition or disease of a patient. In part, embodiments of the present invention are directed to the treatment of neurodegenerative disorders including seizure disorders such as epilepsy.

The term "therapeutically effective amount" means any amount which results in improved treatment, healing, prevention, or amelioration of a disease, disorder, or side effect, or a decrease in the rate of advancement of a disease or disorder. The term also includes within its scope amounts effective to enhance normal physiological function.

The term "$t_{1/2}$" is the time it takes for the plasma concentration to reach half of its original value after administration of the formulation to a subject.

By "$t_{max}$" it is meant the time to reach $C_{max}$ after administration of the formulation to a subject.

The terms "treat," "treated," or "treating" as used herein refer to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

In some embodiments, the compounds and methods disclosed herein can be utilized with or on a subject in need of such treatment, which can also be referred to as "in need thereof." As used herein, the phrase "in need thereof" means that the subject has been identified as having a need for the particular method or treatment and that the treatment has been given to the subject for that particular purpose.

Generally speaking, the term "tissue" refers to any aggregation of similarly specialized cells which are united in the performance of a particular function.

The embodiments set forth herein are described in terms of "comprising", however any embodiment described herein may also be described in terms of "consists of" or "consisting of", meaning that the formulation or method includes only the elements, steps, or ingredients specifically recited in the particular claimed embodiment or claim and each of the embodiments described herein, may also be described in terms of "consisting essentially of" or "consists essentially of", meaning that the formulation or method includes only the specified materials or steps and those that do not materially affect the basic and novel characteristics of the claimed invention.

The term "VEM" means video electroencephalography monitoring.

Pharmaceutical Compositions

Embodiments of the present invention relate to modified release, oral, pharmaceutical compositions of huperzine, and more particularly to huperzine A. Applicants have discovered modified release formulations of huperzine that provide therapeutically effective plasma concentrations of the huperzine, even at high doses given twice daily, and overcome the rapid high peak plasma levels associated with the dose-limiting adverse side effects of huperzine. Exemplary formulations are disclosed in U.S. application Ser. No. 15/985,390 filed May 21, 2018, the disclosure of which is incorporated herein in its entirety by reference.

A dose escalation study conducted by the Applicant (unpublished), indicated that high peak plasma levels greater than about 5 ng/mL especially within the first 31 hours have a high probability of resulting in nausea and vomiting. In the study, 7 out of 8 subjects experienced nausea and/or vomiting within the first 31 hrs. These subjects had an average time to initial nausea of 17.7 hours, and displayed huperzine plasma levels of 4.8 ng/mL on average. The one subject that did not experience nausea did not reach plasma levels of over 5 ng/mL until 42 hours after initial dosing. These findings would indicate that there is a time-concentration relationship, where achieving plasma exposures between 4-5 ng/mL within the first 31 hours may result in drug-related adverse events. Prior to Applicant's immediate release dose escalation study, it was unknown what plasma concentration threshold to stay below in order to obtain a better side effect profile and/or reduced frequency of seizures.

Figure 2:
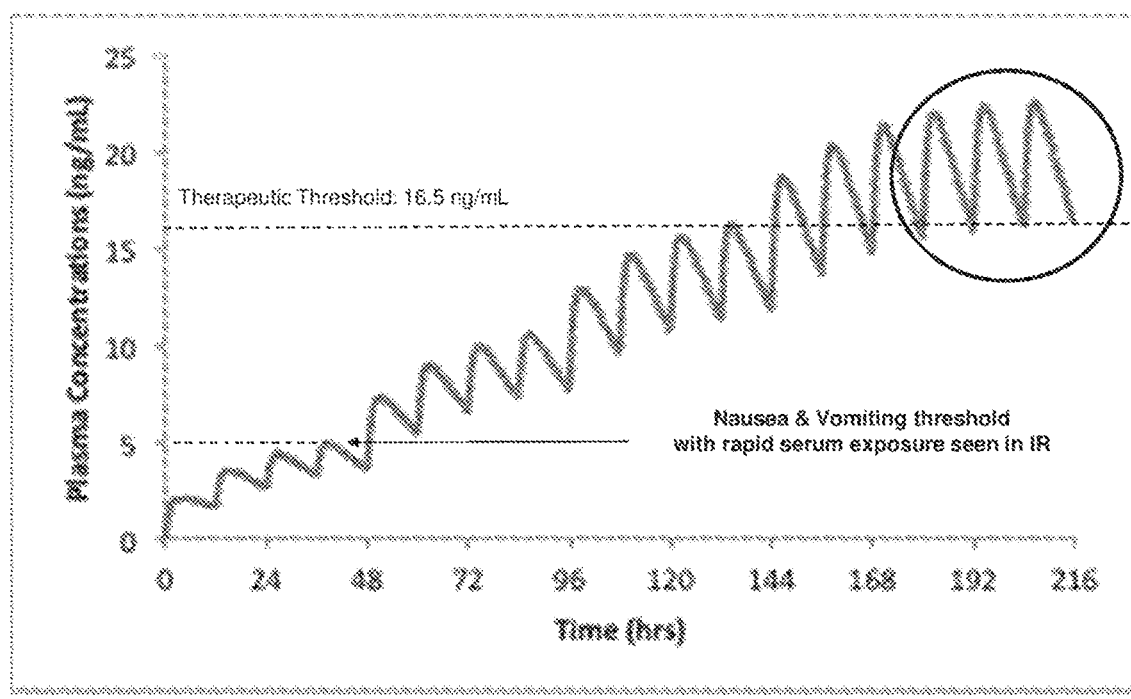
FIG. 2 shows the modeled plasma levels of huperzine A modified release formulation 4A based on a titration schedule of 0.5 mg huperzine A twice a day for days 1-2; 1 mg huperzine A twice a day for days 3-4; 1.5 mg huperzine twice a day for days 5-6 and 2 mg twice a day for days 7-11.

Dosing of about 2 mg of immediate release huperzine A twice a day therefore is predicted to cause early, high plasma peaks associated with nausea and vomiting. Additionally, peak to trough plasma exposures are predicted to fluctuate below the therapeutic threshold. Furthermore, a single missed dose of huperzine is predicted to not only put the subject below the therapeutic threshold, but also expose the subject to rapid, high peak plasma concentration upon resuming the immediate release dose thus potentially resulting in nausea and vomiting each time a dose is missed (FIG. 1). This makes the immediate release formulation unfavorable and potentially dangerous as a therapeutic option. In contrast, the modified release formulations developed by the applicant and administered as described herein, achieved the therapeutic threshold and unlike immediate release formulations, keep plasma exposure levels below the 5 ng/mL threshold initially, thereby avoiding the adverse nausea and vomiting associated with the immediate release formulations. In addition, if, after reaching the therapeutic level, a subject misses a dose, the plasma concentration will not fall so low that the serious adverse events will occur (FIG. 2). Applicant has discussed modified release formulations of huperzine of up to 5 mg/day and up to 2.5 mg BID dose in U.S. patent application Ser. No. 15/985,390; which is incorporated herein by reference in its entirety. However, higher doses of huperzine were considered to be disadvantageous because of increasing dose-limiting adverse effects such as nausea, vomiting and/or diarrhea.

Applicants have now discovered that higher doses of oral pharmaceutical modified release formulations of huperzine offer unexpected, unpredictable properties over other doses of oral pharmaceutical formulations of huperzine. These formulations and dosing regimens allow for significantly higher therapeutic thresholds to be obtained without the side effects associated with high peak plasma levels and also allow for twice daily dosing.

To illustrate the advantages of a modified release formulation of huperzine A in treating, for example, seizure disorders, applicant used non clinical animal data. The applicant generated pharmacokinetic data in dogs (vide infra), allometric scaling, and modeling to determine that a $C_{max}$ of about 16 ng/mL (2.5 mg BID dose) to about 28 ng/mL (4 mg BID dose) of huperzine A in plasma is predicted to achieve significant improvement in efficacy in treating subjects with seizure disorders compared with the 0.5 mg to 2.0 mg BID dose.

Modified release, oral pharmaceutical formulations of huperzine of the present invention comprise a dissolvable core; a huperzine layer coating the dissolvable core; a polymer coating the huperzine layer; and optionally a curable top coat comprising of HPMC or Opadry; wherein the huperzine layer comprises a therapeutically effective amount of huperzine.

In some embodiments of the invention, the dissolvable core is a fully dissolvable core. In further embodiments, the core is a sugar sphere. In some aspects, the sugar sphere comprises sucrose and starch. In some embodiments, the sucrose is at least 62% by weight sucrose. In further embodiments, the sugar spheres are Suglets® sugar spheres. In some aspects, the sugar spheres are of a particle size of about 250 μm to about 1700 μm. In some embodiments, the sugar spheres are selected from a particle size of about 250 μm to about 355 μm, about 500 μm to about 600 μm, about 600 μm to about 710 μm, about 710 μm to about 850 μm, about 850 μm to about 1000 μm, about 850 μm to about 1180 μm, about 1000 μm to about 1180 μm, about 1000 μm to about 1400 μm, about 1400 μm to about 1700 μm and combinations thereof. In further embodiments, the sugar spheres are selected from a particle size of about 500 μm to about 600 μm, or about 600 μm to about 710 μm. In some aspects, the sugar spheres are selected from a particle size of about 500 μm to about 710 μm. In some embodiments, the sugar spheres are Suglets® PF006.

In further embodiments, the sugar sphere comprises about 74 weight % to about 86 weight % of the pharmaceutical composition. In some embodiments, the sugar sphere comprises about 79 weight % to about 84 weight % of the pharmaceutical composition. In some embodiments, the sugar sphere comprises about 80 weight % to about 86 weight % of the pharmaceutical composition. In some embodiments the sugar sphere comprises about 80 weight % to about 83 weight % of the pharmaceutical composition. In some embodiments the sugar sphere comprises about 81 weight % to about 83 weight % of the pharmaceutical composition. In some embodiments the sugar sphere comprises about 81 weight % to about 82.8 weight % of the pharmaceutical composition. In some embodiments the sugar sphere comprises 81.5 weight % to 83.0 weight %. In some embodiments the sugar sphere comprises about 79.1 weight % to about 80 weight % of the pharmaceutical composition. In some embodiments the sugar sphere comprises about 80 weight % to about 81 weight % of the pharmaceutical composition. In some embodiments the sugar sphere comprises about 81 weight % to about 82 weight % of the pharmaceutical composition. In some embodiments the sugar sphere comprises about 81 weight % to about 81.9 weight % of the pharmaceutical composition. In some embodiments the sugar sphere comprises about 81.9 weight % to about 82.8 weight % of the pharmaceutical composition. In some embodiments the sugar sphere comprises about 82 weight % to about 83 weight % of the pharmaceutical composition. In some embodiments the sugar sphere comprises about 82.8 weight % to about 83.7 weight % of the pharmaceutical composition.

In some embodiments the weight percent of sugar sphere in the pharmaceutical composition is between a lower limit of about 74 weight %, about 75 weight %, about 76 weight %, about 77 weight %, 78 about weight %, about 79 weight %, about 80 weight %, about 81 weight %, about 82 weight %, about 83 weight %, about 84 weight %, about 85 weight %, and about 86 weight % and an upper limit of about 86 weight %, about 85 weight %, about 84 weight %, 83 weight %, 82 weight %, 81 weight %, 80 weight %, 79 weight %, 78 weight %, 77 weight %, 76 weight %, 75 weight %, and 74 weight %.

In some embodiments the weight percent of sugar sphere in the pharmaceutical composition is about 74 weight %, about 75 weight %, about 76 weight %, about 77 weight %, 78 about weight %, about 79 weight %, about 80 weight %, about 81 weight %, about 82 weight %, about 83 weight %, about 84 weight %, about 85 weight %, or about 86 weight %.

In some embodiments of the invention, the huperzine layer comprises huperzine A or pharmaceutically acceptable salts thereof. In some embodiments the huperzine A is a huperzia serrata extract. In some embodiments the huperzia serrata extract is 99% huperzine A.

In some aspects, the weight percent of huperzine in the pharmaceutical composition comprises about 0.4 weight % to about 1.5 weight % huperzine or a pharmaceutically acceptable salt of huperzine that is equivalent to 0.4 weight % to about 1.5 weight % huperzine. In some embodiments, the weight percent of huperzine in the pharmaceutical composition comprises about 0.9 weight % to about 1 weight % huperzine or a pharmaceutically acceptable salt of huperzine that is equivalent to 0.9 weight % to about 1 weight % huperzine. In some embodiments, the weight percent of huperzine in the pharmaceutical composition comprises about 0.95 weight % to about 1 weight % huperzine or a pharmaceutically acceptable salt of huperzine that is equivalent to 0.95 weight % to about 1 weight % huperzine. In some embodiments, the weight percent of huperzine in the pharmaceutical composition comprises about 1 weight % huperzine or a pharmaceutically acceptable salt that is equivalent to about 1 weight % huperzine. In some embodiments the weight percent of huperzine in the pharmaceutical composition comprises between a lower limit of about 0.4 weight %, 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % and an upper limit of about 1.5 weight %, about 1.4 weight %, about 1.3 weight %, 1.2 weight %, 1.1 weight %, 1 weight %, 0.9 weight %, 0.8 weight %, 0.7 weight %, 0.6 weight, 0.5 weight % and 0.4 weight % of huperzine or a pharmaceutically acceptable salt of huperzine that is equivalent to a lower limit of about 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % and an upper limit of about 1.5 weight %, about 1.4 weight %, about 1.3 weight %, 1.2 weight %, 1.1 weight %, 1 weight %, 0.9 weight %, 0.8 weight %, 0.7 weight %, 0.6 weight, 0.5 weight % and 0.4 weight % of huperzine. In some embodiments the weight percent of huperzine in the pharmaceutical composition comprises 0.4 weight %, 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % or a pharmaceutically acceptable salt of huperzine that is equivalent to 0.4 weight %, 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % of huperzine. In further embodiments, the huperzine layer comprises a therapeutically effective amount of huperzine.

In some embodiments, the huperzine or pharmaceutically acceptable salt thereof, according to any embodiment described herein, is huperzine A or a pharmaceutically acceptable salt thereof.

In some aspects, the huperzine layer further comprises one or more excipients. In some embodiments, the total amount of excipients is about 5 weight % to about 10 weight % of the pharmaceutical composition. In some embodiments the total amount of excipients is about 5 weight % to about 9 weight % of the pharmaceutical composition. In some embodiments the total amount of excipients is about 5 weight % to about 7 weight % of the pharmaceutical composition. In some embodiments the total amount of excipients in the huperzine layer is selected from about 5 weight %, about 6 weight %, about 7 weight %, about 8 weight %, about 9 weight %, or about 10 weight %, of the pharmaceutical composition. In some embodiments, the excipients are selected from hydroxypropyl methylcellulose or polyvinylpyrrolidone and combinations thereof.

In some embodiments, the hydroxypropyl methylcellulose is a low viscosity or very low viscosity hydroxypropyl methylcellulose, such as, for example Methocel™. In further embodiments, the hydroxypropyl methylcellulose is Methocel VLV or the like. In some aspects, the amount of hydroxypropyl methylcellulose in the huperzine layer is about 6 weight % to about 7 weight % of the composition. In some aspects, the amount of hydroxypropyl methylcellulose in the huperzine layer is about 5 weight % to about 6 weight % of the composition. In some embodiments, the amount of hydroxypropyl methylcellulose in the huperzine layer is about 6 weight %. In some embodiments, the amount of hydroxypropyl methylcellulose in the huperzine layer is about 5 weight %. In further embodiments, the hydroxypropyl methylcellulose is Methocel VLV and the amount of Methocel VLV in the huperzine layer is about 6.1 weight % of the composition.

In some embodiments of the invention, the polyvinylpyrrolidone is any polyvinylpyrrolidone appropriate for use in an oral formulation. In further embodiments, the polyvinyl pyrrolidone is polyvinylpyrrolidone K30. In some aspects, the amount of polyvinylpyrrolidone in the huperzine layer is about 0.5 weight % to about 1.5 weight % of the composition. In some embodiments, the polyvinylpyrrolidone in the huperzine layer is about 0.95 weight % to about 1 weight % of the composition. In some embodiments, the polyvinylpyrrolidone in the huperzine layer is about 0.90 weight % to about 1 weight % of the composition. In some embodiments, the polyvinylpyrrolidone in the huperzine layer is about 1 weight % of the composition. In further embodiments the polyvinylpyrrolidone is polyvinylpyrrolidone K30 and the amount of polyvinylpyrrolidone K30 in the huperzine layer is about 1 weight % of the composition.

In some embodiments the one or more excipients in the huperzine layer is a combination of hydroxypropyl methylcellulose and polyvinylpyrrolidone. In some embodiments the one or more excipients in the huperzine layer is of about 5 weight % to about 7 weight % hydroxypropyl methylcellulose and about 0.5 weight % to about 1.5 weight % polyvinylpryrrolidone. In some embodiments the one or more excipients in the huperzine layer is about 6 weight % hydroxypropyl methylcellulose and about 1 weight % polyvinylpyrrolidone.

In some embodiments of the invention, the polymer coating is a poly acrylamide polymer or ethylcellulose polymer layer coating the huperzine layer. In some embodiments the polymer coating is a non-polyacrylamide polymer coating the huperzine layer. In some embodiments the polymer coating is a plasticized ethylcellulose polymer layer coating the huperzine layer. In further embodiments the plasticized ethylcellulose is Surelease®. In some aspects the plasticized ethylcellulose is Surelease® Type B NF.

In some embodiments the plasticized ethylcellulose polymer comprises about 7 weight % to about 16 weight % of the composition. In some embodiments the plasticized ethylcellulose polymer comprises about 8 weight % to about 13 weight % of the composition. In some embodiments the plasticized ethylcellulose polymer comprises about 7 weight % to about 12 weight % of the composition. In some embodiments the plasticized ethylcellulose polymer comprises about 8 weight % to about 12 weight % of the composition. In some embodiments the plasticized ethylcellulose polymer comprises about 9 weight % to about 11 weight % of the composition. In some embodiments the plasticized ethylcellulose polymer comprises about 9 weight % to about 10 weight % of the composition. In some embodiments the plasticized ethyl cellulose polymer comprises about 8.3 weight % to about 9.2 weight % of the pharmaceutical composition. In some embodiments the plasticized ethyl cellulose polymer comprises about 9.2 weight % to about 10.1 weight % of the pharmaceutical composition. In some embodiments the plasticized ethyl cellulose polymer comprises about 10.1 weight % to about 11 weight % of the pharmaceutical composition. In some embodiments the plasticized ethyl cellulose polymer comprises about 11 weight % to about 12 weight % of the pharmaceutical composition. In some embodiments the plasticized ethyl cellulose polymer comprises about 12 weight % to about 12.9 weight % of the pharmaceutical composition. In some embodiments the plasticized ethyl cellulose polymer comprises about 15 weight % to about 16 weight % of the pharmaceutical composition.

In some embodiments, the weight percent of plasticized ethylcellulose polymer in the composition is between a lower limit of 7 weight %, 8 weight %, 9 weight %, 10 weight %, 11 weight %, 12 weight %, 13 weight %, 14 weight %, 15 weight %; and 16 weight % and an upper limit of 16 weight %, 15 weight %, 14 weight %; 13%, 12 weight %, 11 weight %, 10 weight %, 9 weight %, 8 weight % and 7 weight %.

In some embodiments, the pharmaceutical composition for oral delivery comprises:
  a) a dissolvable core according to any embodiment described herein for dissolvable cores;
  b) a huperzine layer comprising huperzine or a pharmaceutically acceptable salt of huperzine, according to any embodiment described herein for the huperzine layer, huperzine or a pharmaceutically acceptable salt of huperzine, coating the dissolvable core; and c) a polymer coating, coating the huperzine layer according to any embodiment described herein; and d) optionally a curable top coat layer coating the polymer layer and comprising HPMC or Opadry seal coat.

In some aspects of the invention the pharmaceutical composition for oral delivery comprises: (a) about 74 weight % to about 86 weight % of a sugar sphere core wherein the sugar sphere core has a particle size of about 500-710 µm; (b) a huperzine layer coating the sugar sphere, wherein the huperzine layer comprises about 0.95 to about 1 weight % huperzine or a pharmaceutically acceptable salt of huperzine that is equivalent to about 0.95 to about 1 weight % huperzine, and one or more excipients, wherein the total amount of excipients is about 5 weight % to about 9 weight %, (c) about 7 weight % to about 16 weight % of a plasticized ethyl cellulose polymer layer coating the huperzine layer, wherein the huperzine layer comprises a therapeutically-effective amount of huperzine. In further aspects, the huperzine is huperzine A. In further embodiments the one or more excipients is a combination of hydroxypropyl methylcellulose and polyvinylpyrrolidone. In further embodiments the one or more excipients is a combination of about 6 weight % hydroxypropyl methylcellulose and about 1 weight % polyvinylpyrrolidone. In some embodiments the hydroxypropyl methylcellulose is a low viscosity hydroxypropyl methylcellulose, the polyvinylpyrrolidone is a polyvinylpyrrolidone K30 and the plasticized ethyl cellulose is Surelease® Type B NF.

In some aspects of the invention the pharmaceutical composition for oral delivery comprises: (a) about 79 weight % to about 84 weight % of a sugar sphere core wherein the sugar sphere core has a particle size of about 500-710 µm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % of huperzine, about 6 weight % hydroxypropyl methylcellulose, and 0.95 to about 1 weight % polyvinylpryrrolidone; and (c) about 8 weight % to about 13 weight % of a plasticized ethyl cellulose polymer layer coating the huperzine layer, wherein the huperzine layer comprises a therapeutically-effective amount of huperzine. In further aspects, the huperzine is huperzine A. In further aspects, the huperzine is huperzine A, the hydroxypropyl methylcellulose is a low viscosity hydroxypropyl methylcellulose, the polyvinylpyrrolidone is polyvinylpyrrolidone K30 and the plasticized ethyl cellulose is Surelease® Type B NF, the hydroxypropyl methylcellulose is a low viscosity hydroxypropyl methylcellulose, the polyvinylpyrrolidone is a polyvinylpyrrolidone K30 and the plasticized ethyl cellulose is Surelease® Type B NF.

In some aspects of the invention the pharmaceutical composition for oral delivery comprises: (a) about 80 weight % to about 83 weight % of a sugar sphere core wherein the sugar sphere core has a particle size of about 500-710 µm; (b) a huperzine layer coating the sugar sphere, wherein the huperzine layer about 0.95 weight % to about 1 weight % huperzine or a pharmaceutically acceptable salt of huperzine that is equivalent to about 0.95 weight % to about 1 weight % huperzine, about 5 weight % to about 6 weight % hydroxypropyl methylcellulose, and about 0.95 weight % to about 1 weight % polyvinylpryrrolidone; and (c) about 8 weight % to about 12 weight % of a plasticized ethyl cellulose polymer layer coating the huperzine layer, wherein the huperzine layer comprises a therapeutically-effective amount of huperzine. In further aspects, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is Surelease® Type B NF.

In some aspects of the invention the pharmaceutical composition for oral delivery comprises: (a) about 81 weight % to about 82 weight % of a sugar sphere core wherein the sugar sphere core has a particle size of about 500-710 µm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % of huperzine, about 5 weight % to about 6 weight % hydroxypropyl methylcellulose, and about 0.95 weight % to about 1 weight % polyvinylpryrrolidone; and (c) about 10 weight % to about 11 weight % of a plasticized ethyl cellulose polymer layer coating the huperzine layer, wherein the huperzine layer comprises a therapeutically-effective amount of huperzine. In further aspects, the huperzine is huperzine A, the hydroxypropyl methylcellulose is a low viscosity hydroxypropyl methylcellulose, the polyvinylpyrrolidone is polyvinylpyrrolidone K30 and the plasticized ethyl cellulose is Surelease® Type B NF.

In some aspects of the invention the pharmaceutical composition for oral delivery comprises: (a) about 81.5 weight % of a sugar sphere core wherein the sugar sphere core has a particle size of about 500-710 µm; (b) a huperzine layer coating the sugar sphere, wherein the huperzine layer comprises about 1 weight % huperzine or a pharmaceutically acceptable salt of huperzine that is equivalent to 1 weight % of huperzine, about 5.9 weight % hydroxypropyl methylcellulose, and about 1 weight % polyvinylpryrrolidone; and (c) about 10.7 weight % of a plasticized ethyl cellulose polymer layer coating the huperzine layer, wherein the huperzine layer comprises a therapeutically-effective amount of huperzine. In further aspects, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is Surelease® Type B NF.

In some aspects of the invention the pharmaceutical composition for oral delivery comprises: (a) about 82 weight % to about 83 weight % of a sugar sphere core wherein the sugar sphere core has a particle size of about 500-710 µm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % of huperzine, about 5 weight % to about 6 weight % hydroxypropyl methylcellulose, and about 0.95 weight % to about 1 weight % polyvinylpryrrolidone; and (c) about 9 weight % to about 10 weight % of a plasticized ethyl cellulose polymer layer coating the huperzine layer, wherein the huperzine layer comprises a therapeutically-effective amount of huperzine. In further aspects, the huperzine is huperzine A, the hydroxypropyl methylcellulose is a low viscosity hydroxypropyl methylcellulose, the polyvinylpyrrolidone is polyvinylpyrrolidone K30 and the plasticized ethyl cellulose is Surelease® Type B NF.

In some aspects of the invention the pharmaceutical composition for oral delivery comprises: (a) about 83 weight % of a sugar sphere core wherein the sugar sphere core has a particle size of about 500-710 µm; (b) a huperzine layer coating the sugar sphere, wherein the huperzine layer comprises about 1 weight % huperzine or a pharmaceutically acceptable salt of huperzine that is equivalent to 1 weight % of huperzine, about 6 weight % hydroxypropyl methylcellulose, and about 1 weight % polyvinylpryrrolidone; and (c) about 9 weight % of a plasticized ethyl cellulose polymer layer coating the huperzine layer, wherein the huperzine layer comprises a therapeutically-effective amount of huperzine. In further aspects, the huperzine is huperzine A, the hydroxypropyl methylcellulose is a low viscosity hydroxypropyl methylcellulose, the polyvinylpyrrolidone is polyvinylpyrrolidone K30 and the plasticized ethyl cellulose is Surelease® Type B NF.

In some aspects of the invention the pharmaceutical composition for oral delivery according to any embodiment described herein further comprises a seal coat layer in between the huperzine layer and the plasticized ethyl cellulose layer.

In some aspects of the invention the pharmaceutical composition for oral delivery according to any embodiment described herein further comprises a top coat layer over the seal coat layer. In some embodiments, the top coat layer may include a curable composition comprising HPMC, Surelease, or Opadry.

Some embodiments describe a pharmaceutical composition for oral delivery comprising: (a) about 75 weight % to about 76 weight % of a sugar sphere core wherein the sugar sphere core has a particle size of about 500-710 μm; (b) a huperzine layer coating the sugar sphere, wherein the huperzine layer comprises about 0.9 weight % to about 1 weight % huperzine or a pharmaceutically acceptable salt of huperzine that is equivalent to about 0.9 weight % to about 1 weight % of huperzine, about 5 weight % to about 6 weight % hydroxypropyl methylcellulose, and about 0.9 weight % to about 1 weight % polyvinylpryrrolidone; (c) a seal coat layer coating the huperzine layer, comprising about 1 weight % to about 2 weight % hydroxypropylmethyl cellulose; and (d) about 15 weight % to about 16 weight % of a plasticized ethyl cellulose polymer layer coating the huperzine layer, wherein the huperzine layer comprises a therapeutically-effective amount of huperzine. In further aspects, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is Surelease® Type B NF.

Some embodiments describe a pharmaceutical composition according to any embodiment described herein, that exhibits the following dissolution profile when tested according to USP type 1 dissolution apparatus at 50 revolutions per minute in 50 mM phosphate buffer (pH 6.8) at 37° C.: about 36% of the huperzine is released after 2 hours, about 63% of the huperzine is released after 4 hours, about 84% of the huperzine is released after 8 hours and not less than about 89% of the huperzine is released after 12 hours. In some embodiments the huperzine is huperzine A.

Some embodiments describe a pharmaceutical composition according to any embodiment described herein, that exhibits the following dissolution profile when tested according to USP type 1 dissolution apparatus at 50 revolutions per minute in 50 mM phosphate buffer (pH 6.8) at 37° C.: about 46% of the huperzine is released after 2 hours, about 77% of the huperzine is released after 4 hours, about 97% of the huperzine is released after 8 hours and not less than about 99% of the huperzine is released after 12 hours. In some embodiments the huperzine is huperzine A.

The pharmaceutical compositions of the invention are formulated for oral administration and can be, for example, in the form of tablets, sprinkles, capsules and pills. In one aspect, the pharmaceutical compositions according to any embodiment described herein, are formulated for oral administration in the form of capsules. In some aspects, the pharmaceutical compositions according to any embodiment described herein, are formulated for oral administration in the form of tablets. The compositions of the inventions can contain additional non-toxic pharmaceutically acceptable carriers and/or diluents and/or adjuvants and/or excipients. The use of such media and agents for pharmaceutically active substances is well known in the art and includes tablet binders, lubricants, flavoring agents, preservatives, wetting agents, emulsifying agents, and dispersing agents.

As illustrated below and in the examples that follow, Applicants have shown that the compositions and methods described in any of the embodiments described herein, have unexpected and unpredictable properties. For example, Applicants surprisingly and unexpectedly discovered that patients dosed with about 3.0 mg BID to about 4.0 mg BID doses of huperzine compositions described herein demonstrated exceptionally improved seizure control. In some cases, the patients showed an increased seizure reduction from the 2.5 mg BID dose, without any of the side effects or dose-limiting adverse effects. In some cases, the patients showed an increased seizure reduction of about 90% or more, about 92% or more, about 95% or more, and even total elimination of seizures.

For the studies, Applicants used compositions comprising an inert core layer, a huperzine layer coating the core layer and a polymer layer coating the huperzine layer as shown in Table 1.

TABLE 1

| Composition No. | Core type/Size* Weight % of total composition | Huperzine Layer ** Weight % of each component in total composition | Seal coat layer Weight % of each component in total composition | Polymer layer Weight % of total composition |
| --- | --- | --- | --- | --- |
| 4A | 82.95 Sugar spheres 500-710 μm | 5.97 HPMC 1 PVP 1 Huperzine A | | 9.09 Surelease |
| 4B | 79.34 Sugar spheres 500-710 μm | 5.71 HPMC 0.95 PVP 0.95 Huperzine A | | 13.04 Surelease |
| 4D | 82.95 Sugar spheres 500-710 μm | 5.97 HPMC 1 PVP 1 Huperzine A | | 9.09 Surelease |
| 4C | 91.24 Sugar spheres 500-710 μm | 6.57 HPMC 1.09 PVP 1.09 Huperzine A | | 0% |

TABLE 1-continued

| Composition No. | Core type/Size* Weight % of total composition | Huperzine Layer ** Weight % of each component in total composition | Seal coat layer Weight % of each component in total composition | Polymer layer Weight % of total composition |
| --- | --- | --- | --- | --- |
| 4E | 75.81 Sugar spheres 500-710 μm | 5.46 HPMC 0.91 PVP 0.91 Huperzine A | 1.66 HPMC | 15.35 Surelease |
| 4F1 | 81.47 Sugar spheres 500-710 μm | 5.87 HPMC 0.98 PVP 0.98 Huperzine A | | 10.71 Surelease |
| 4F2 | 81.47 Sugar spheres 500-710 μm | 5.87 HPMC 0.98 PVP 0.98 Huperzine A | | 10.71 Surelease |

*MCC = Microcrystalline cellulose spheres
** HPMC = hydroxypropylmethyl cellulose; PVP = polyvinylpyrrolidone Methods of Treatment The pharmaceutical compositions according to any embodiment described herein, are useful in treating neurological disorders, including seizure disorders to a patient in need thereof. They can be administered therapeutically to treat, prevent, or slow the rate of onset of neuronal dysfunctions. Some embodiments describe methods of treating neurological disorders and a seizure disorder. Some embodiments describe methods of treating neurological disorders selected from amyloid-related disorder such as Alzheimer's disease and the amyloid-disorders described herein, psychiatric disorders such as Tourette's syndrome, post-traumatic stress disorder (PTSD), panic and anxiety disorders, obsessive-compulsive disorder, and schizophrenia, developmental disorders such as fragile X syndrome and autism, pain, drug addictions such as alcoholism, neurodegenerative diseases such as Parkinson's disease and Huntington's disease, as well as stroke and ischemic brain injury, amyotrophic lateral sclerosis, epilepsy, and any disorder, symptom, or effect associated with or relating to exposure to a neurotoxin, including but not limited to neurotoxins such as chemical warfare agents, with a pharmaceutical composition according to any embodiment described herein.

In some aspects, the present invention provides methods of treating seizures or seizure disorders selected from epilepsy (including intractable epilepsy), generalized seizures, primary generalized seizures, absence seizures, myoclonic seizures, partial seizures, complex partial seizures with or without generalization (for example, focal impaired awareness seizures (FIAS)), Lennox-Gastaut Syndrome, Dravet Syndrome and Generalized Epilepsy with Febrile Seizures plus (GEFS+). In some embodiments, the seizure disorder is epilepsy.

The pharmaceutical composition according to any embodiment described herein, can be administered therapeutically to treat, prevent, or slow the rate of onset of neuronal dysfunctions, such as epilepsy and seizures, or prophylactically to either protect against further seizures associated with epilepsy or to avoid or forestall the onset of seizures associated with other disorders. For example, the pharmaceutical compositions according to any embodiment described herein, can be administered prophylactically to slow or halt the progression of seizures and epilepsy in a patient who has had a stroke and has a risk of developing seizure as a result of the stroke.

Further embodiments describe methods of treating epilepsy, intractable epilepsy and FIAS, comprising administering to a patient in need thereof, a pharmaceutical composition according to any embodiment described herein.

In some embodiments the pharmaceutical composition of the invention is administered at a dose to reduce the frequency of seizures by at least 10% with few or no side effects. Preferably, the reduction is greater than about 70%, 75%, 80%, 85%, 90%, 95% or seizures are eliminated. For example, the pharmaceutical compositions and methods according to any embodiment described herein, prevents the development of or complete elimination of seizures.

In further aspects, the present invention provides methods of treating any disorder, symptom, or effect associated with or related to exposure to a neurotoxin, including but not limited to neurotoxins such as chemical warfare agents, comprising administering to a patient in need thereof, a pharmaceutical composition according to any embodiment described herein.

In some embodiments, the dose of the pharmaceutical compositions of the invention preferably does not exceed 15 mg/day. In some embodiments, the dose of the pharmaceutical compositions of the invention preferably does not exceed 20 mg/day. In some embodiments the daily dose according to any embodiment described herein, is administered twice a day. In some embodiments the dose is about 1.5 mg twice a day to about 5.0 mg twice a day. In some embodiments the dose is about 3.0 mg twice a day to about 4.0 mg twice a day. In some embodiments the dose is about 2.75 mg twice a day, about 3.0 mg twice a day, about 3.25 mg twice a day, about 3.50 mg twice a day, about 3.75 mg twice a day, about 4.0 mg twice a day, 4.5 mg twice a day, 4.75 mg twice a day or 5.0 mg twice a day. In yet other embodiments, the dose is 5.5, 6.0, 6.5, 7.0, 7.5, 8.0, 8.5, 9.0, 9.5 or 10 mg twice a day.

In some embodiments, for example, to treat symptoms, or effect associated with or relating to exposure to a neurotoxin, including but not limited to neurotoxins such as chemical warfare agents, doses of about 2.75 mg twice a day to about 5.0 mg twice a day, about 3.0 mg twice a day to about 4.75 mg twice a day, about 3.25 mg twice a day to about 4.5 mg twice a day, about 3.5 mg twice a day to about 4.25 mg twice a day, about 3.75 mg twice a day to about 4.0 mg twice a day, or about 3 mg twice a day to about 4 mg twice a day may also be used.

In some embodiments the present disclosure provides a method of treating a neurological or seizure disorder comprising administering to a patient in need thereof, one or more titration doses of a modified release formulation of huperzine, followed by a maintenance dose of an oral modified release formulation of huperzine, wherein the patient has a better side effect profile and/or reduced frequency of seizures. In some embodiments, the titration dose comprises about 0.5 mg BID to about 2.5 mg BID. In some embodiments, the titration dose comprises from about 0.25 mg twice a day to about 2.5 mg twice a day, about 0.5 mg twice a day to about 2.5 mg twice a day, about 0.5 mg twice a day to about 2.0 mg twice a day, about 0.75 mg twice a day to about 1.75 mg twice a day, or about 1.0 mg twice a day to about 1.5 mg twice a day, and ranges between any two of these values or less than any one of these values. In some embodiments, the maintenance dose comprises about 3.0 mg BID to about 4.0 mg BID. In some embodiments, the maintenance dose may comprise from about 2.75 mg twice a day to about 5.0 mg twice a day, about 3.0 mg twice a day to about 4.75 mg twice a day, about 3.25 mg twice a day to about 4.5 mg twice a day, about 3.5 mg twice a day to about 4.25 mg twice a day, about 3.75 mg twice a day to about 4.0 mg twice a day, or about 3 mg twice a day to about 4 mg twice a day, and ranges between any two of these values or less than any one of these values. In some embodiments, the titration dose may comprise one or more of about 0.5 mg twice a day, about 0.75 mg twice a day, about 1.75 mg twice a day, about 2.5 mg twice a day, and the maintenance dose may comprise one or more of about 2.5 mg twice a day, about 2.75 mg twice a day, about 3.0 mg twice a day, about 3.25 mg twice a day, about 3.5 mg twice a day, about 3.75 mg twice a day, and about 4.0 mg twice a day, and values between any two of these values or less than any one of these values.

In some embodiments the present disclosure provides a method of treating a neurological or seizure disorder comprising administering to a patient in need thereof, a therapeutically effective amount of a modified release formulation of huperzine. In some embodiments, the therapeutically effective amount of huperzine comprises twice a day dose of about 3.0 mg to about 4.0 mg. This includes about 2.75 mg twice a day, about 3.0 mg twice a day, about 3.25 mg twice a day, about 3.5 mg twice a day, about 3.75 mg twice a day, and about 4.0 mg twice a day, and values between any two of these values or less than or greater than any one of these values.

In some embodiments the present disclosure provides a method of treating a disorder selected from a neurological disorder or a seizure disorder, comprising administering to a patient in need thereof, a pharmaceutical composition for oral delivery comprising about 74 weight % to about 86 weight % of a sugar sphere core wherein the sugar sphere core has a particle size of about 500-710 μm; a huperzine layer coating the sugar sphere, wherein the huperzine layer comprises about 0.95 to about 1 weight % huperzine or a pharmaceutically acceptable salt of huperzine that is equivalent to about 0.95 to about 1 weight % huperzine, and one or more excipients, wherein the total amount of excipients is about 5 weight % to about 9 weight %; about 7 weight % to about 16 weight % of a plasticized ethyl cellulose polymer layer coating the huperzine layer, wherein the huperzine layer contains a therapeutically effective amount of huperzine. In some embodiments, the therapeutically effective amount of huperzine comprises twice a day dose of about 3.0 mg to about 4.0 mg. This includes about 2.75 mg BID, about 3.0 mg BID, about 3.25 mg BID, about 3.5 mg BID, about 3.75 mg BID, and about 4.0 mg BID, and values between any two of these values or less than or greater than any one of these values.

In some embodiments of the methods described herein, the seizure disorder is selected from epilepsy and focal impaired awareness seizure. In some embodiments, the seizure disorder is focal impaired awareness seizure (FIAS).

Figure 7:
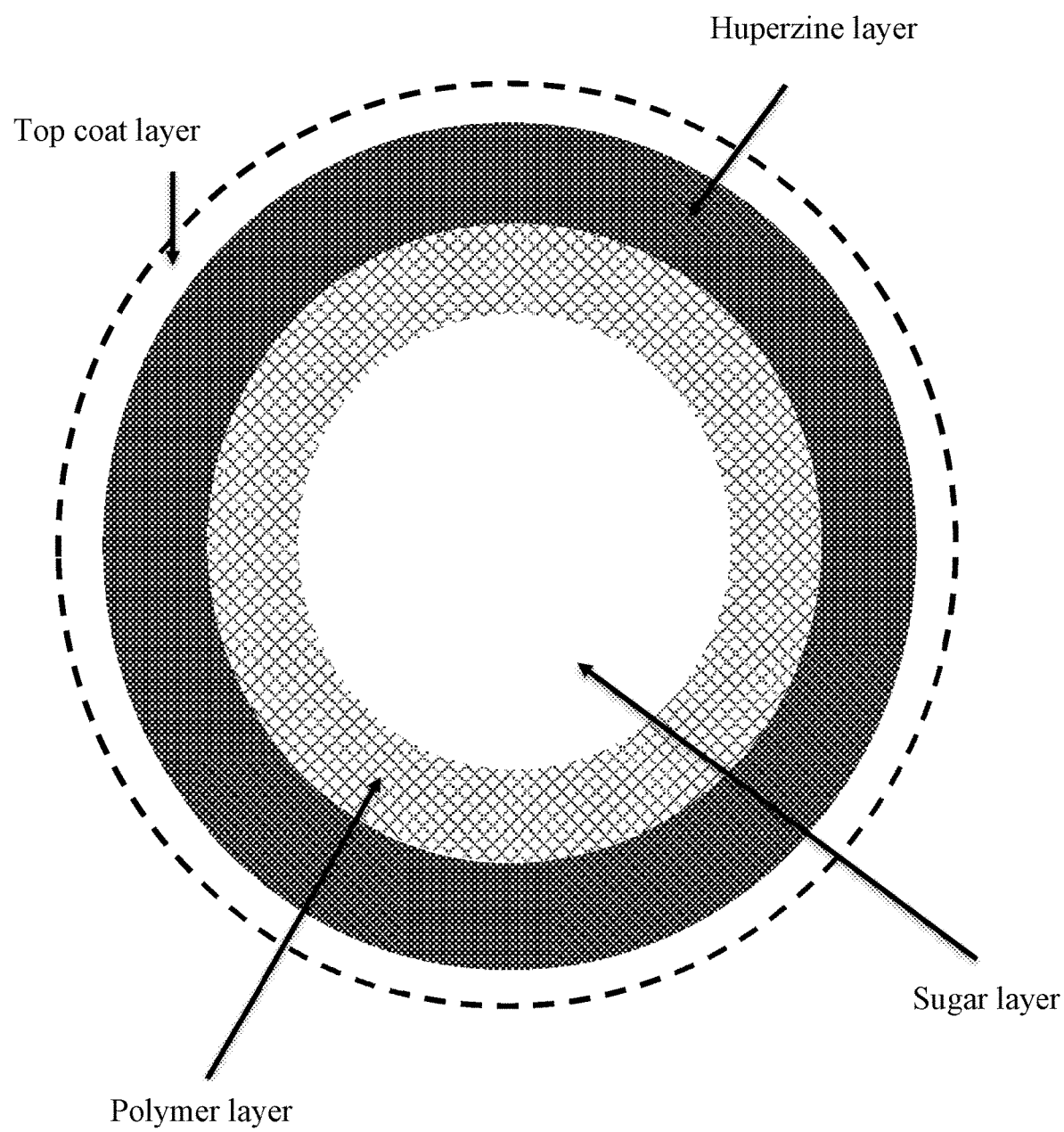
FIG. 7 is a schematic of the composition of the invention.

In some embodiments the present disclosure provides a method of treating a neurological or seizure disorder comprising administering to a patient in need thereof, one or more titration doses of a modified release formulation of huperzine, followed by a maintenance dose of an oral modified release formulation of huperzine, wherein the patient has a better side effect profile and/or reduced frequency of seizures. In some embodiments, the modified release formulation of huperzine administered in the titration dose is the same modified release formulation of huperzine administered in the maintenance dose. In further embodiments, the modified release formulation of huperzine administered in the titration dose is different than the modified release formulation of huperzine administered in the maintenance dose. In further embodiments the huperzine is huperzine A. In some embodiments the modified release formulation of huperzine is as shown in FIG. 7, and comprises a dissolvable core; an active huperzine A layer coating the dissolvable core; a polymer coating, coating the huperzine A layer; and optionally a curable top coat layer comprising HPMC or Opadry. In further embodiments, the modified release huperzine formulation is a pharmaceutical composition according to any embodiment described herein. In some embodiments, the modified release formulation of huperzine is a pharmaceutical composition according to any embodiment described herein, and is the same pharmaceutical composition in the titration dose and the maintenance dose. In some embodiments, the oral modified release formulation of huperzine is a pharmaceutical composition comprising huperzine A according to any embodiment described herein, and is the same pharmaceutical composition comprising huperzine A in the titration dose and the maintenance dose. In some embodiments, the dose is titrated from a low dose to high dose over several days to several weeks until a maintenance dose is reached.

Some embodiments describe a method of treating a neurological disorder or a seizure disorder, in a patient in need thereof, wherein the patient has a better side effect profile and/or reduced frequency of seizures, comprising administering a first dosing regimen of at least one dosing regimen selected from a. to i. (as further described below) and administering a second dosing regimen of at least one dosing regimen selected from j. to o. (as further described below), provided the second dosing regimen ascends from the first dosing regimen and further provided the last dosing regimen is the maintenance dose and therefore will be administered for as long as the patient is in need of treatment thereof:

a. optionally administering a dose of about 0.25 mg of huperzine A, once every about 12 hours for at least two days and up to two weeks;
b. optionally administering a dose of about 0.5 mg of huperzine A, once every about 12 hours for at least two days and up to two weeks;
c. optionally administering a dose of about 0.75 mg of huperzine A, once every about 12 hours for at least two days and up to two weeks;
d. optionally administering a dose of about 1 mg of huperzine A, once every about 12 hours for at least two days and up to two weeks;
e. optionally administering a dose of about 1.25 mg of huperzine A, once every about 12 hours for at least two days and up to two weeks;
f. optionally administering a dose of about 1.5 mg of huperzine A, once every about 12 hours for at least two days and up to two weeks;
g. optionally administering a dose of about 1.75 mg of huperzine A, once every about 12 hours for at least two days and up to two weeks;

h. optionally administering a dose of about 2 mg of huperzine A, once every about 12 hours for at least two days and up to two weeks;
i. optionally administering a dose of about 2.5 mg of huperzine A, once every about 12 hours for at least two days;
j. optionally administering a dose of about 2.75 mg of huperzine A, once every about 12 hours for at least two days;
k. optionally administering a dose of about 3.0 mg of huperzine A, once every about 12 hours for at least two days;
l. optionally administering a dose of about 3.25 mg of huperzine A, once every about 12 hours for at least two days;
m. optionally administering a dose of about 3.5 mg of huperzine A, once every about 12 hours for at least two days;
n. optionally administering a dose of about 3.75 mg of huperzine A, once every about 12 hours for at least two days;
o. optionally administering a dose of about 4.0 mg of huperzine A, once every about 12 hours for at least two days;

wherein the huperzine of a.-o. is administered in a modified release formulation.

In further embodiments the modified release formulation is a pharmaceutical composition according to any embodiment described herein. In further embodiments the huperzine is huperzine A. In further embodiments each dose prior to the maintenance dose is administered for 2 days to two weeks. It will be understood that any combination of at least one dosing regimen selected from a. to i. and at least one dosing regimen selected from j. to o., allows for any combination of dosing regimens and thus describes a minimum of two dosing regimens (1 initial dose lower than the maintenance dose and 1 maintenance dose) and a maximum of 14 dosing regimens (ascending dosing regimens a. through i. and maintenance dose j. through n.

In some embodiments the method comprises administering any dosing regimen selected from the following (wherein the last designated dose is the maintenance dose):

In some embodiments, the method comprises
a. administering a dose of about 0.5 mg of huperzine A, once every about 12 hours for at least 2 days;
b. administering a dose of about 0.75 mg of huperzine A, once every about 12 hours for at least 2 days;
c. administering a dose of about 1.75 mg of huperzine A, once every about 12 hours for at least 2 days;
d. administering a dose of about 3.0 mg of huperzine A, once every about 12 hours for at least two days.

In some embodiments step d. is administered for as long as the patient is in need of treatment.

In some embodiments, the method further comprises after step d.:
e. administering a dose of about 3.25 mg of huperzine A once every about 12 hours for as long as the patient is in need thereof.

In some embodiments, the method further comprises after step d.:
e. administering a dose of about 3.25 mg of huperzine A once every about 12 hours for at least 2 days;
f. administering a dose of about 3.5 mg of huperzine A once every about 12 hours for at least 2 days;

In some embodiments, the method further comprises after step d.:
e. administering a dose of about 3.25 mg of huperzine A once every about 12 hours for at least 2 days;
f. administering a dose of about 3.5 mg of huperzine A once every about 12 hours for at least 2 days;
g. administering a dose of about 3.75 mg of huperzine A once every about 12 hours for as long as the patient is in need thereof.

In some embodiments, the method further comprises after step d.:
e. administering a dose of about 3.25 mg of huperzine A once every about 12 hours for at least 2 days;
f. administering a dose of about 3.5 mg of huperzine A once every about 12 hours for at least 2 days;
g. administering a dose of about 3.75 mg of huperzine A once every about 12 hours for at least 2 days;
h. administering a dose of about 4.0 mg of huperzine A once every about 12 hours for as long as the patient is in need thereof.

| | | | | | |
|---|---|---|---|---|---|
| a to o; | a to n; | a to m; | a to l; | a to k; | a to j; |
| a, c to o; | a, c to n; | a, c to m; | a, c to l; | a, c to k; | a, c to j; |
| a, c to j; | a, c, d, k; | a, b, d to i; | a, b, d to k; | a, b, d to k; | a, b, d to o; |
| a, b, d, e, o; | a, b, d, k; | a to c, e to o; | a to c, e to k; | a to c, e to g; | a to c, e, f; |
| a to c, e; | a to d, f to o; | a to d, f to k; | a to d, f to g; | a to d, f; | a to e, g to o; |
| a to e, g, k; | a to e, g; | a to f, k, o; | a to f, k; | a to g, o; | b to o; |
| b to o; | b to n; | b to m; | b to l; | b to m; | b, d to o; |
| b, d to k; | b, d to g; | b, d to f; | b, d, e; | b, d; | b, c, e to o; |
| b, c, e to k; | b, c, e to g; | b, c, e, f; | b, c, e; | b, c; | b to d, f to o; |
| b to d, f to k; | b to d, f, g; | b to d, f; | b to e, g to o; | b to e, g, k; | b to e, g; |
| b to f, k, o; | b to f, k; | b to g, o; | c to o; | c to k; | c to g; |
| c to f; | c to e; | c, d; | c, e to o; | c, e to k; | c, e to g; |
| c, e, f; | c, e; | c, d, f to o; | c, d, f to k; | c, d, f, g; | c, d, f; |
| c to e, g to o; | b to e, g, n; | c to e, g ; | c to f, k, o; | c to f, k; | c to g, o |
| b, c, g, i, o; | b, c, g, i, n; | b, c, g, i, m; | b, c, g, i, l; | b, c, g, i, k; | b, c, g, i, j; |
| a to d, f, h, i, k, m, o | b, d, f | b, d, f, g | b, d, f, g, h | b, d, f, h | b, d, f, h, 2.25 mg |
| | b, d, f, h, i | b, d, f, h, i, k | b, d, f, h, i, k, m | b, d, f, h, i, k, m, o | |
| b, d, g, i, o; | b, d, g, i, n; | b, d, g, i, m; | b, d, g, i, l; | b, d, g, i, k; | b, d, g, i, j; |
| b, d, g, i | b, d, g, i | | | | |
| b, d, h, o | b, d, h, n | b, d, h, m | b, d, h, l | b, d, h, k | b, d, h, j |
| b, d, h, i | | | | | |

Some embodiments of the present disclosure are directed to a method of treating a neurological disorder or a seizure disorder, in a patient in need thereof, wherein the patient has a better side effect profile and/or reduced frequency of seizures, comprising administering a modified release formulation (4F1/4F2) of huperzine A, wherein the modified release formulation of huperzine A is characterized by a Css of huperzine in plasma for the following selected doses:

| Dose (mg) | Css (ng/mL) |
|---|---|
| 2.5 | about 7.43 to about 9.08 |
| 2.75 | about 8.19 to about 10.0 |
| 3.0 | about 9.0 to about 11.0 |
| 3.25 | about 9.8 to about 12.0 |
| 3.5 | about 10.7 to about 13.1 |
| 3.75 | about 11.6 to about 14.2 |
| 4.0 | about 12.5 to about 15.3 |

In further embodiments the modified release formulation is a pharmaceutical composition according to any embodiment described herein.

Some embodiments describe a method of treating a neurological disorder or seizure disorder, to a patient in need thereof, wherein the patient has a better side effect profile, comprising administering a modified release formulation of huperzine A, wherein the modified release formulation of huperzine is characterized by a Css of huperzine in plasma of about 0.6 ng/mL to about 12 ng/mL when administered at a therapeutically effective dose. In some embodiments the Css of huperzine in plasma is about 2 ng/mL to about 12 ng/mL when administered at a therapeutically effective dose. In some embodiments the Css of huperzine in plasma is about 4 ng/mL to about 12 ng/mL when administered at a therapeutically effective dose. In some embodiments the Css of huperzine in plasma is about 6 ng/mL to about 12 ng/mL when administered at a therapeutically effective dose. In some embodiments the Css of huperzine in plasma is about 4 ng/mL to about 10 ng/mL when administered at a therapeutically effective dose. In some embodiments the Css of huperzine in plasma is about 4 ng/mL to about 8 ng/mL when administered at a therapeutically effective dose. In some embodiments the Css of huperzine in plasma is about 6.4 ng/mL to about 10 ng/mL when administered at a therapeutically effective dose. In some embodiments the Css of huperzine in plasma is about 8 ng/mL when administered at a therapeutically effective dose. In some embodiments the Css of huperzine in plasma is at least 8 ng/mL when administered at a therapeutically effective dose. In further embodiments the huperzine is huperzine A. In further embodiments the modified release formulation is a pharmaceutical composition according to any embodiment described herein.

Some embodiments of the present disclosure are directed to a method of treating a neurological or seizure disorder comprising administering to a patient in need thereof, a modified release formulation of huperzine. In some embodiments the huperzine is huperzine A. In some embodiments the modified release formulation of huperzine is a pharmaceutical composition according to any embodiment described herein. In some embodiments the modified huperzine formulation is formulation 4F1/4F2.

The pharmaceutical compositions of the present invention can be administered in a combination with other therapeutic agent(s). The choice of therapeutic agents that can be co-administered with the composition of the invention will depend, in part, on the condition being treated. For example, the compounds of the invention can be administered in combination with other agents, such as acetaminophen, ibuprofen, naproxen, carisoprodol, chlorozoxazone, cyclobenzaprine, metaxalone, methocarbamol, orphenadrine, tizanidine, baclofen, dantrolene, diazepam, citalopram, escitalopram, fluoxetine, paroxetine, sertraline, duloxetine, venlafaxine, imipramine, hydroxyzine, propranolol, gabapentin, pregabalin, alprazolam, clonazepam, chlordiazepoxide, lorazepam, buspirone, modafinil, armodafinil, ethosuximide, valproic acid, levetiracetam, lacosamide, eslicarbazepine, carbamazepine, oxcarbazepine, phenytoin, fosphenytoin, topiramate, CGRP inhibitors, flunarizine, cannabinoids and/or lamotrigine used to treat other symptoms and side effects commonly associated with epilepsy or seizures, such as fainting, fatigue, muscle spasms, auras, amnesia, anxiety, depression, headaches, sleepiness, or staring spells.

Such other therapeutic agent(s) may be administered prior to, simultaneously with or following the administration of huperzine pharmaceutical composition according to any embodiment described herein.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples. The following examples are for illustrative purposes only and are not to be construed as limiting the invention in any manner.

Example 1

Evaluation of the Bioavailability, Safety and Tolerability of Modified Release Huperzine a Following Multiple Dose Administrations in Healthy Subjects A single center, on-site/outpatient, dose escalation study was conducted with oral pharmaceutical composition 4D. The healthy volunteers were dosed twice daily (BID) in a cohort of 8 subjects (Formulation 4D) to assess plasma levels, safety, and allow necessary dosing alterations to occur prior to dosing any subsequent subjects. The study was conducted in an on-site setting at dose initiation and at times of dose escalation to evaluate safety, and for specimen collection for routine laboratory and pharmacokinetic analysis. Subjects were discharged and compliance of BID dosing was monitored via twice daily phone calls by site staff. The initial dose was 0.5 mg BID with a dose escalation every 2-3 days until a maximum tolerated dose was observed or a maximum of 2.5 BID dose was obtained. Initial dose and rate of escalation was able to be altered at the discretion of the site staff to ensure safety of the subjects.

Study Endpoints: Plasma concentration data was used for bioavailability assessment. The derived pharmacokinetic parameters include: area under the curve (AUC), maximum plasma concentration (Cmax), and time of $C_{max}$ (Tmax).

The safety and tolerability parameters were assessed based on the occurrence of adverse events as well as the results of study-specified vital signs, neurological and physical examinations, ECG evaluations, and clinical laboratory studies.

Dosing schedule was as follows:

Cohorts 1 & 2 (Formulation 4D):

| Days 1, 2 | Days 3, 4 | Days 5, 6, 7 | Days 8, 9 | Days 10, 11 |
|---|---|---|---|---|
| 0.5 mg BID | 1 mg BID | 1.5 mg BID | 2.0 mg BID | 2.5 mg BID |

Cohort 3 (Formulation 4D):

| Days 1, 2 | Days 3, 4 | Days 5, 6, 7 | Days 8, 9 | Days 10, 11 | Days 12, 13, 14 |
|---|---|---|---|---|---|
| 0.25 mg BID | 0.5 mg BID | 1 mg BID | 1.5 mg BID | 2 mg BID | 2.5 mg BID |

Cohort 4 (Formulation 4D):

| Days 1, 2 | Days 3, 4 | Days 5, 6, 7 | Days 8, 9 | Days 10, 11 | Days 12, 13, 14 | Days 15, 16 | Day 17, 18 |
|---|---|---|---|---|---|---|---|
| 0.25 mg BID | 0.5 mg BID | 0.75 mg BID | 1 mg BID | 1.25 mg BID | 1.5 mg BID | 1.75 mg BID | 2.0 mg BID |

Cohorts 5 and 6 (Formulation 4E):

| Days 1, 2 | Days 3, 4 | Days 5, 6, 7 | Days 8, 9 | Days 10, 11 | Days 12, 13, 14 | Days 15, 16 | Day 17, 18 |
|---|---|---|---|---|---|---|---|
| 0.25 mg BID | 0.5 mg BID | 0.75 mg BID | 1 mg BID | 1.25 mg BID | 1.5 mg BID | 1.75 mg BID | 2.0 mg BID |

Figure 3:
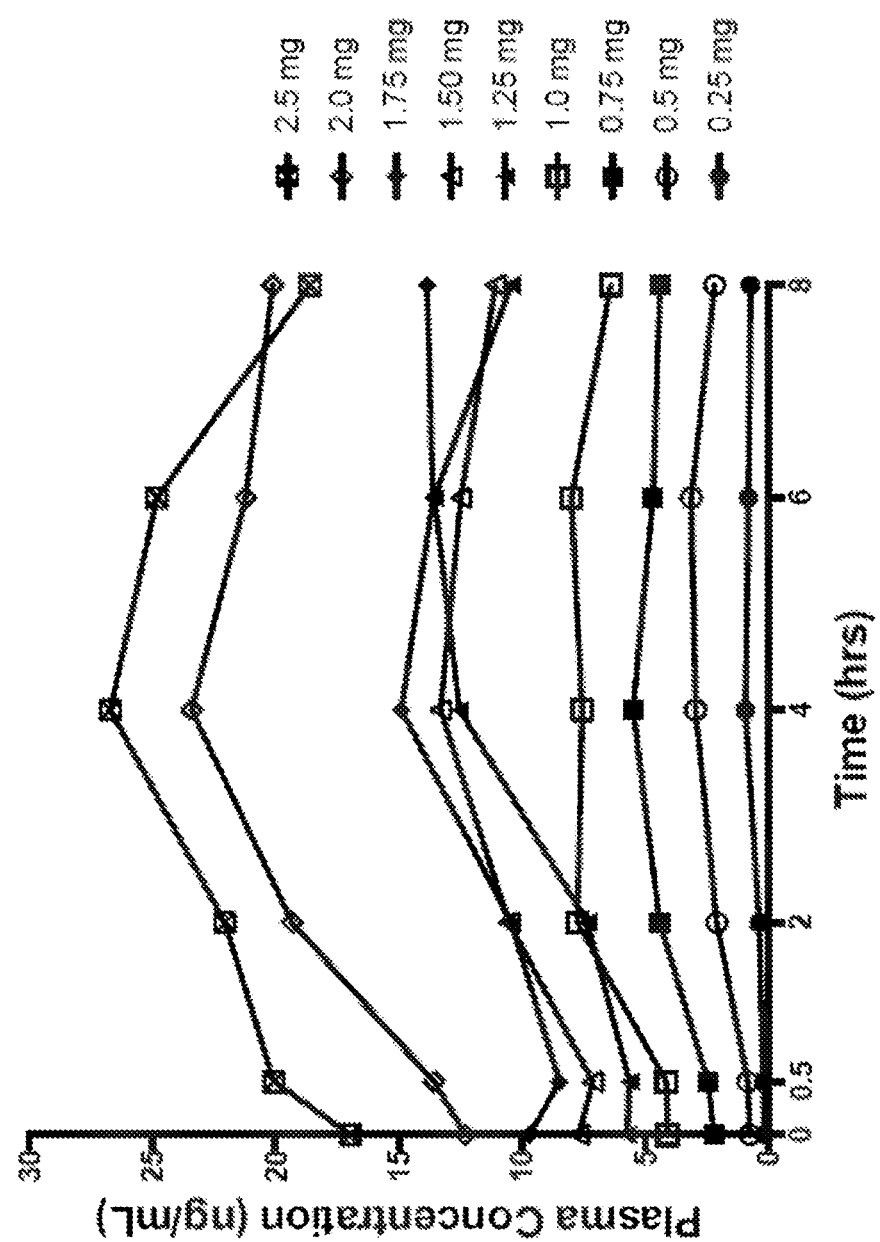
FIG. 3 shows the in vivo plasma concentration in healthy subjects over time taken during dose titration from 0.25 mg to 2.5 mg of the pharmaceutical composition 4D.

Plasma levels taken on dose titration inpatient days throughout the study for cohorts 1-4 are shown in FIG. 3. Plasma draws occurred throughout the dose titration schedule to assess total plasma concentrations. Time=0 represents pre-dose baseline on the titration day corresponding to the dosing schedule. Means reflect all data obtained for 8 subjects. The initial dosing schedule was altered for cohorts 3 and 4 to accommodate a slower titration (0.25 mg dose increments).

Figure 4:
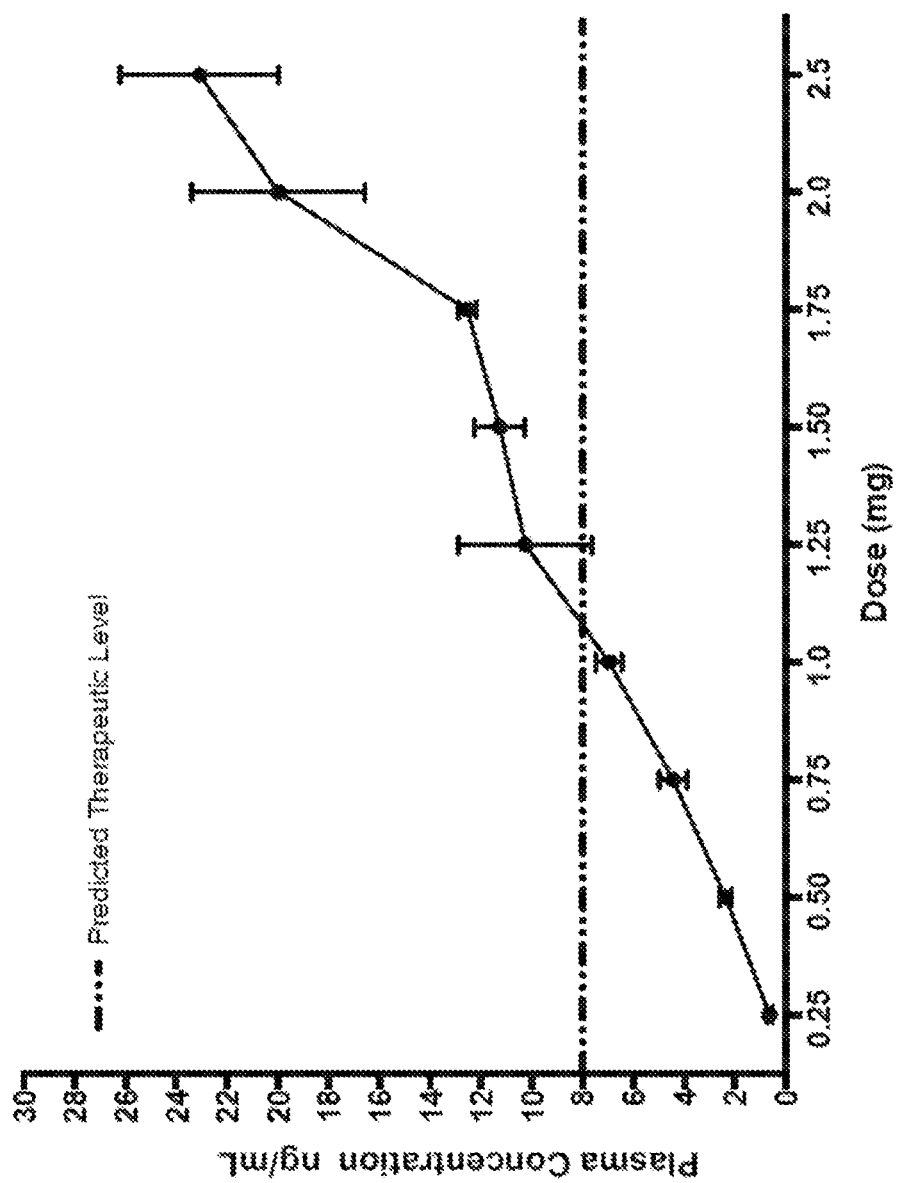
FIG. 4 shows the in vivo plasma concentration ($C_{ss}$) in healthy humans at various doses of the pharmaceutical composition 4D.

A graph of the average plasma levels taken on inpatient days throughout the study at particular doses is shown in FIG. 4. Pharmacokinetic modeling predicts average plasma level (Css) of 8.4 ng/mL to achieve 100% seizure protection in 50% of patients (dosing equivalent to about 1.1-1.25 mg BID.

The compositions in the study yielded favorable pharmacokinetic profiles, demonstrated twice a day dosing and demonstrated a dramatic reduction in adverse events when compared to immediate release preparation, even with double the dose previously used. Pharmacokinetic modeling accurately predicted dose-exposure relationships for the entire dose titration.

Adverse events were mild and transient. Testing showed that approximately double the dose predicted for significant seizure control was attainable; yielding much higher, stable plasma levels of huperzine A given on a twice a day schedule, and achieved drug plasma levels predicted to provide significant seizure protection in patients with adult and childhood intractable epilepsies.

Example 2

Evaluation of Safety and Efficacy of Modified Release Formulations of Huperzine for the Treatment of Adult Focal Impaired Awareness Seizures (FIAS)

The purpose of this study is to examine safety signals and demonstrate seizure reduction in adults with FIAS treated with modified release formulations of huperzine as an add-on therapy in an in-patient and out-patient study with the pharmaceutical composition according to any embodiment described herein. In some embodiments the pharmaceutical composition is 4F1 or 4F2.

Dose administration for each participant will begin at 0.25 mg BID escalating sequentially every 4 days to a maximum tolerated dose or target dose of 1.75 mg BID. Participants who are unable to tolerate a dose during dose escalation will have their dose reduced to the prior tolerable dose; if unable to tolerate lower doses, participants will be withdrawn from the study.

Planned Number of Participants:

Sixteen participants will be enrolled into and complete the study.

Study Design:

This study is a single center, multi-site, open-label, add-on study in otherwise healthy participants with frequent Focal Impaired Awareness Seizures.

Pre-qualified, eligible participants age 18 and older that have signed an informed consent will be enrolled into the study. The study will consist of a 96-hour baseline continuous VEM period, a one-month out-patient dose escalation treatment period, followed by a second 96-hour continuous VEM treatment period.

On Day 1 of the baseline period (after completion of physical and neurological exams, vital signs, electrocardiogram (ECG), blood sample for CBC and chemistry, urine sample collection for standard urinalysis including creatinine and electrolytes) daily seizure counting will begin and will be collected via VEM with standard lead placement. Participants will remain on stable anticonvulsant treatment regimen as determined by their treating physician. Upon completion of the baseline period (5 days in-patient VEM), participants who experienced at least 5 focal impaired awareness seizures will be immediately enrolled into treatment. They will begin dose escalation of modified release huperzine to either the target dose of 3.0 mg BID, 4.0 mg BID or a maximum tolerated dose. The modified release huperzine will be titrated over 28 days, escalating every 4 days. Upon reaching the target dose or maximum tolerated dose, participants will begin a 96-hour in-patient VEM treatment period. After the inpatient VEM treatment period, participants will have the option to escalate dose further, per investigator discretion, up to a maximum tolerated dose, or a dose in which seizures are eliminated completely, and maintain that dose for the balance of the out-patient titration period. A daily seizure diary will be kept for the duration of the out-patient titration period where participants or caregivers will notate seizure type and time of day. Participants who are unable to attain target dose of 3.0 mg BID or 4.0 mg BID will be dose reduced to a prior tolerable dose. If unable to tolerate lower doses, participants may be withdrawn from the study. Participants will be dosed 2 times daily (every 12 hrs) with the modified release huperzine, administration occurring in the morning and evening. Participants will have formulation 4F1/4F2 discontinued at the final day of in-patient VEM unless they elect to participate in the open-label extension period, during which they will continue to record seizure diaries and will have safety assessments on a regular basis.

Blood samples for pharmacology will be drawn on selected out- and in-patient study days. Adverse events (AE) and use of concurrent medications will be recorded throughout the study.

All participants who receive at least one dose of investigational product will be included in safety analyses that includes vital signs, clinical laboratory testing, physical and neurological examinations, electrocardiograms and adverse event monitoring.

Endpoint:

Primary Efficacy Variables: Reduction in average daily seizure count between baseline (pre-treatment) and evaluation (on treatment) VEM periods.

Secondary Efficacy Variables:

Percent reduction in average daily seizure count from the baseline VEM period compared to the evaluation VEM period (on treatment)

Percent reduction in average number of seizures from the baseline period (screening/retrospective diary) compared to the last week of the titration treatment period Percent of participants considered treatment responders defined as those with a ≥25%, ≥50%, ≥75%, ≥90%, reduction in seizures from the baseline VEM period compared to the VEM treatment evaluation period Percent of reduction of average number of seizures vs. baseline/retrospective diary at 1, 3, 6, 12 months during the extension period Proportion of subjects with 100% seizure reduction Proportion of subjects requiring rescue medication at different dosages Pharmacology:

Plasma concentration data will be used to determine a dose, plasma level and seizure effect relationship.

Urine samples will undergo standard urinalysis, test drug elimination and presence of potential metabolites.

Figure 5:
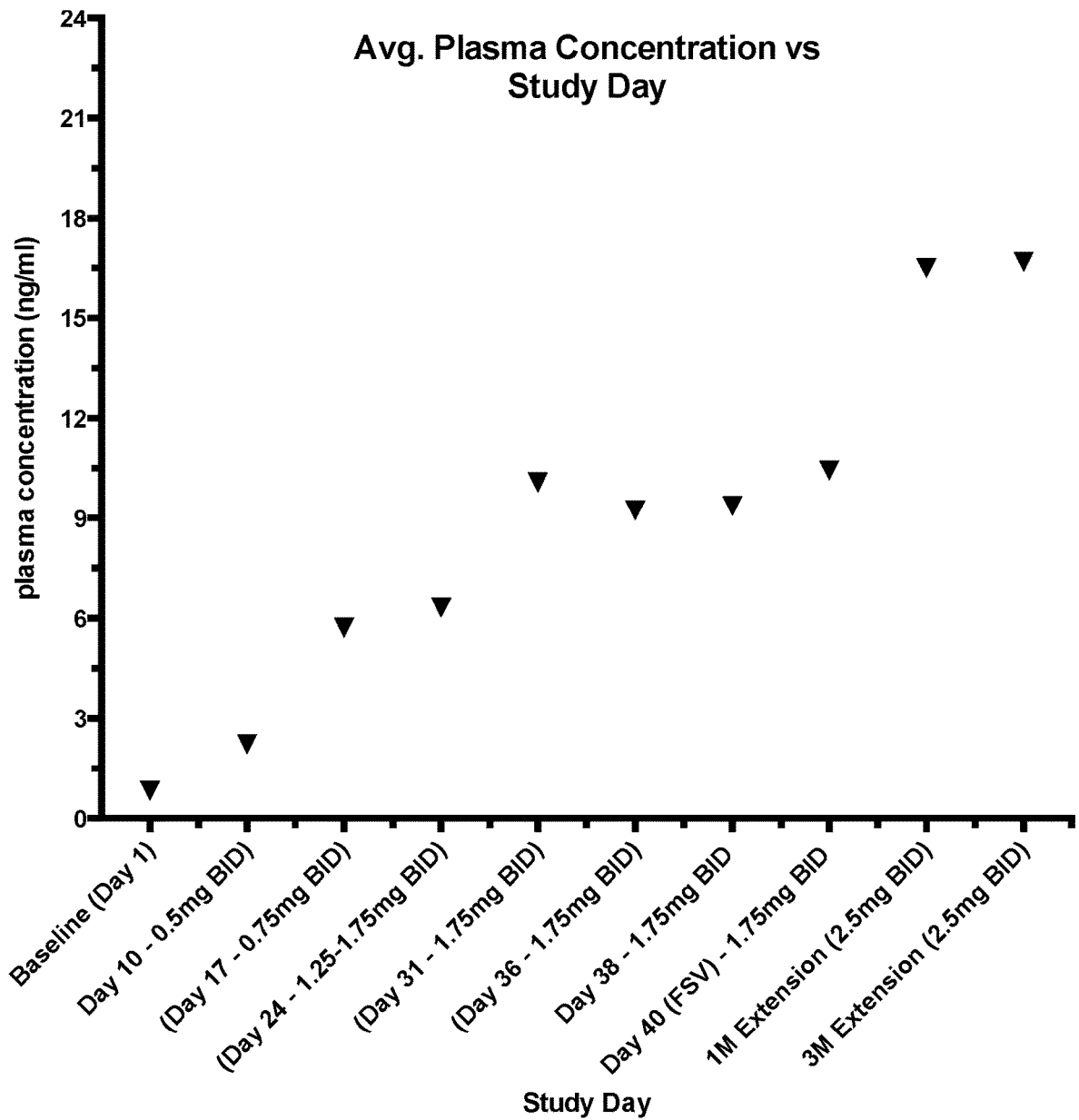
FIG. 5 shows the average in vivo plasma concentration for three human patients taken during dose titration of 0.5 mg, 0.75 mg, 1.25-1.75 mg, and 2.5 mg BID using formulation 4F1/4F2.

To date three patients have received dose titrations as described in FIG. 5 which also shows associated average plasma concentrations.

Figure 6A:
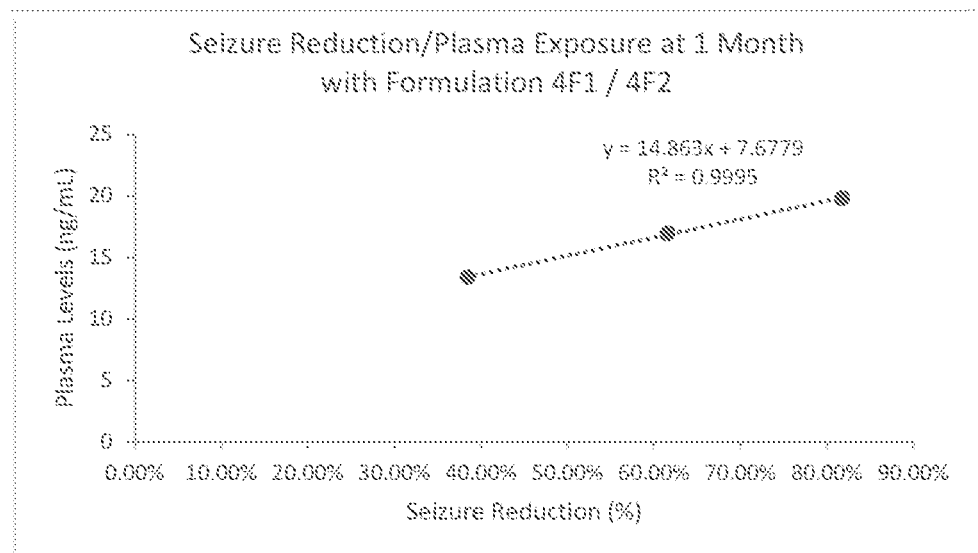
FIGS. 6A and 6B show plots of plasma levels vs. seizure counts for three human patients.
Figure 6B:
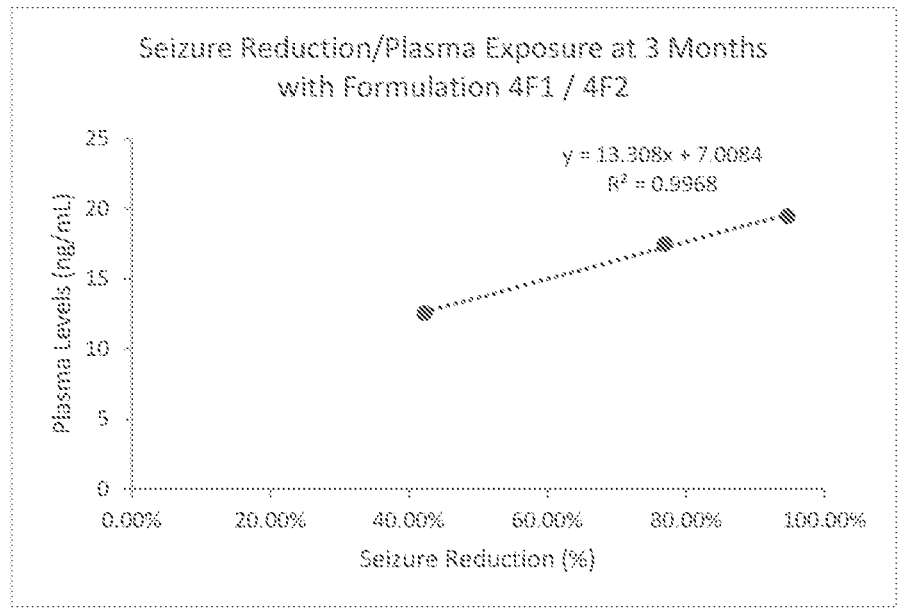

FIGS. 6A and 6B show a plot of plasma values vs. seizure control from the FIAS trial, correlated to seizure counts to assess an exposure effect at reducing seizures. The plot represents single PK draws taken at 4 hrs (Tmax) after the morning dose, and seizure counts are based on a 28-day period. The figures shows a clear correlation between exposure and protection against seizures.

The seizure counts for subjects 1001, 1002 and 2001 for baseline vs extension phase dose of 3 mg BID is shown in Table 2 below.

TABLE 2

| | | Total Seizure Counts | | |
|---|---|---|---|---|
| | Dose BID | Subject 1001 | Subject 1002 | Subject 2001 |
| Baseline Seizure Frequency (per 28 days) | 0 | 13 | 151 | 26 |
| Extension at 2.5 mg | 2.5 | 4 | 53 | 15 |
| 2.5 mg at 1 month | 2.5 | 5 | 26 | 16 |
| 2.5 mg at 3 months | 2.5 | 3 | 8 | 15 |
| Extension at 3.0 mg | 3.0 | 1 | 11 | — |

Example 3

General Procedure for the Preparation of Pharmaceutical Compositions

The pharmaceutical compositions described herein can generally be prepared as follows:
i. Utilizing a fluid bed coating equipment (or similar coated particle manufacturing equipment), use standard procedures and operating conditions to manufacture coated particles. These procedures include:
ii. Prepare solutions for manufacturing the modified release particles, e.g. solutions containing huperzine, binders, anti-caking agents, etc.
iii. Load uncoated cores into fluid bed
iv. Adjust all operating parameters nozzles, pressures, to appropriate ranges for the appropriate batch size and equipment being utilized
v. Process coated pellets to remove agglomerates or fine particles outside of the desired particle size distribution.

An exemplary process comprises:
1. Solution Preparation
a. Heat up predetermined amount of distilled water to 70° C.
b. Dissolve huperzine into anhydrous ethanol by stirring.
c. Add HPMC into the heated water with continuous stirring when needed.
d. Add another partitioned amount of distilled water into the above solution;
keep stirring until the powders are fully dissolved.
e. Add PVP into HPMC solution and equally make it dissolve by continuous stirring.
f. Combine HMPC/PVP solution with the huperzine ethanol solution. Flush the vessel using distilled water and carefully pour into the solution until the final weight is targeted and keep stirring for another 5 min.
2. Drug Layer Coating
Sucrose spheres of the desired size were transferred into a fluidized bed processor and the aforesaid huperzine solution of 1. f were coated onto the sucrose spheres at the product temperature of 3545° C.
3. Sustained Release Layer Coating
Plasticized ethyl cellulose solution that had been prepared ahead were coated onto the resultant huperzine loaded sugar spheres using the same product temperature range above until the theoretical weight gain target was achieved.
4. Top Coat Layer Coating
A top layer coating of HPMC or Opadry may be applied as described above on top of the sustained release layer coating.

The invention claimed is:
1. A method of treating a disorder selected from a neurological disorder or a seizure disorder, comprising administering to a patient in need thereof, a pharmaceutical composition for oral delivery comprising:
about 74 weight % to about 86 weight % of a sugar sphere core wherein the sugar sphere core has a particle size of about 500-710 μm;
a huperzine layer coating the sugar sphere, wherein the huperzine layer comprises about 0.4 to about 1 weight % huperzine or a pharmaceutically acceptable salt of huperzine that is equivalent to about 0.95% to about 1 weight % huperzine, and one or more excipients, wherein the total amount of excipients is about 5 weight % to about 9 weight %;

about 7 weight % to about 16 weight % of a plasticized ethyl cellulose polymer layer coating the huperzine layer, wherein the huperzine layer contains a therapeutically effective amount of huperzine;

wherein the pharmaceutical composition comprises an amount of huperzine of about 0.25 mg to about 4.0 mg, wherein the pharmaceutical composition is administered to the patient BID, and wherein the BID administration of the oral pharmaceutical composition provides an in vivo steady-state concentration ($C_{ss}$) of huperzine in plasma of about 0.52 ng/mL to about 38 ng/mL.

2. The method of claim 1, wherein the seizure disorder is selected from epilepsy and focal impaired awareness seizure.

3. The method of claim 1, wherein the seizure disorder is focal impaired awareness seizure.

4. The method of claim 1, wherein said administration comprises administering one or more titration doses of the pharmaceutical composition followed by administering a maintenance dose of the pharmaceutical composition, wherein the titration dose comprises about 0.5 mg BID to about 2.5 mg BID; and wherein the maintenance dose comprises about 3.0 mg BID to about 4.0 mg BID.

5. The method of claim 1, comprising administering a first dosing regimen of at least one dosing regimen selected from a. to i. and administering a second dosing regimen of at least one dosing regimen selected from j. to o., provided the second dosing regimen ascends from the first dosing regimen and further provided the last dosing regimen is the maintenance dose and therefore will be administered for as long as the patient is in need of treatment thereof:
 a. optionally administering a dose of about 0.25 mg of huperzine A, once every about 12 hours for at least two days;
 b. optionally administering a dose of about 0.5 mg of huperzine A, once every about 12 hours for at least two days;
 c. optionally administering a dose of about 0.75 mg of huperzine A, once every about 12 hours for at least two days;
 d. optionally administering a dose of about 1 mg of huperzine A, once every about 12 hours for at least two days;
 e. optionally administering a dose of about 1.25 mg of huperzine A, once every about 12 hours for at least two days;
 f. optionally administering a dose of about 1.5 mg of huperzine A, once every about 12 hours for at least two days;
 g. optionally administering a dose of about 1.75 mg of huperzine A, once every about 12 hours for at least two days;
 h. optionally administering a dose of about 2 mg of huperzine A, once every about 12 hours for at least two days;
 i. optionally administering a dose of about 2.5 mg of huperzine A, once every about 12 hours for at least two days;
 j. optionally administering a dose of about 2.75 mg of huperzine A, once every about 12 hours for at least two days;
 k. optionally administering a dose of about 3.0 mg of huperzine A, once every about 12 hours for at least two days;
 l. optionally administering a dose of about 3.25 mg of huperzine A, once every about 12 hours for at least two days;
 m. optionally administering a dose of about 3.5 mg of huperzine A, once every about 12 hours for at least two days;
 n. optionally administering a dose of about 3.75 mg of huperzine A, once every about 12 hours for at least two days;
 o. optionally administering a dose of about 4.0 mg of huperzine A, once every about 12 hours for at least two days;
 wherein the huperzine A of a.-o. is administered in the pharmaceutical composition of claim 1; and
 wherein the method reduces the frequency of one or more adverse events selected from the group consisting of nausea, vomiting, and diarrhea.

6. The method of claim 5, comprising:
 a. administering a dose of about 0.5 mg of huperzine A, once every about 12 hours for at least two days;
 b. administering a dose of about 0.75 mg of huperzine A, once every about 12 hours for at least two days;
 c. administering a dose of about 1.75 mg of huperzine A, once every about 12 hours for at least two days;
 d. administering a dose of about 3.0 mg of huperzine A, once every about 12 hours for at least two days.

7. The method of claim 6, wherein step d is administered for as long as the patient is in need of treatment.

8. The method of claim 6, further comprising after step d:
 e. administering a dose of about 3.25 mg of huperzine A once every about 12 hours for as long as the patient is in need thereof.

9. The method of claim 6, further comprising after step d.:
 e. administering a dose of about 3.25 mg of huperzine A once every about 12 hours for at least two days;
 f. administering a dose of about 3.5 mg of huperzine A once every about 12 hours for as long as the patient is in need thereof.

10. The method of claim 6, further comprising after step d.:
 e. administering a dose of about 3.25 mg of huperzine A once every about 12 hours for at least two days;
 f. administering a dose of about 3.5 mg of huperzine A once every about 12 hours for at least two days;
 g. administering a dose of about 3.75 mg of huperzine A once every about 12 hours for as long as the patient is in need thereof.

11. The method of claim 6, further comprising after step d.:
 e. administering a dose of about 3.25 mg of huperzine A once every about 12 hours for at least two days;
 f. administering a dose of about 3.5 mg of huperzine A once every about 12 hours for at least two days;
 g. administering a dose of about 3.75 mg of huperzine A once every about 12 hours for at least two days;
 h. administering a dose of about 4.0 mg of huperzine A once every about 12 hours for as long as the patient is in need thereof.

12. A method of reducing the frequency of seizures in a patient in need thereof, comprising administering to the patient a pharmaceutical composition comprising a therapeutically effective amount of huperzine, the pharmaceutical composition comprising:
 about 74 weight % to about 86 weight % of a sugar sphere core wherein the sugar sphere core has a particle size of about 500-710 μm;

a huperzine layer coating the sugar sphere, wherein the huperzine layer comprises about 0.4 to about 1 weight % huperzine or a pharmaceutically acceptable salt of huperzine that is equivalent to about 0.95% to about 1 weight % huperzine, and one or more excipients, wherein the total amount of excipients is about 5 weight % to about 9 weight %;

about 7 weight % to about 16 weight % of a plasticized ethyl cellulose polymer layer coating the huperzine layer, wherein the huperzine layer contains a therapeutically effective amount of huperzine;

wherein the pharmaceutical composition comprises an amount of huperzine of about 0.25 mg to about 4.0 mg, wherein the pharmaceutical composition is administered to the patient BID, and wherein the BID administration of the oral pharmaceutical composition provides an in vivo steady-state concentration ($C_{ss}$) of huperzine in plasma of about 0.52 ng/mL to about 38 ng/mL.

* * * * *